US009573908B2

(12) United States Patent
Bassler et al.

(10) Patent No.: US 9,573,908 B2
(45) Date of Patent: Feb. 21, 2017

(54) BROAD SPECTRUM PRO-QUORUM-SENSING MOLECULES AS INHIBITORS OF VIRULENCE IN VIBRIOS

(71) Applicants:Bonnie L. Bassler, Princeton, NJ (US); Wai-Leung Ng, Lawrenceville, NJ (US); Lark J. Perez, Ewing, NJ (US); Jianping Cong, Plainsboro, NJ (US); Martin F. Semmelhack, Princeton, NJ (US)

(72) Inventors: Bonnie L. Bassler, Princeton, NJ (US); Wai-Leung Ng, Lawrenceville, NJ (US); Lark J. Perez, Ewing, NJ (US); Jianping Cong, Plainsboro, NJ (US); Martin F. Semmelhack, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 14/381,432

(22) PCT Filed: Feb. 20, 2013

(86) PCT No.: PCT/US2013/026837
§ 371 (c)(1),
(2) Date: Aug. 27, 2014

(87) PCT Pub. No.: WO2014/092751
PCT Pub. Date: Jun. 19, 2014

(65) Prior Publication Data
US 2015/0126474 A1 May 7, 2015

Related U.S. Application Data

(60) Provisional application No. 61/603,590, filed on Feb. 27, 2012.

(51) Int. Cl.
*C07D 253/075* (2006.01)
*A61K 31/53* (2006.01)
*A61P 31/04* (2006.01)
*A01N 43/707* (2006.01)
*A01N 55/00* (2006.01)
*C07F 7/10* (2006.01)

(52) U.S. Cl.
CPC ....... *C07D 253/075* (2013.01); *A01N 43/707* (2013.01); *A01N 55/00* (2013.01); *A61K 31/53* (2013.01); *C07F 7/10* (2013.01)

(58) Field of Classification Search
CPC ... C07D 253/07; C07D 253/075; A61K 31/53
USPC .......................................... 544/182; 514/242
See application file for complete search history.

(56) References Cited

U.S. PATENT DOCUMENTS 4,067,979 A 1/1978 Bickel et al.
6,777,420 B2 8/2004 Zhi et al.

OTHER PUBLICATIONS

Singh S.B., Bioorganic & Medicinal Chemistry Letters 24 (2014) 3683-3689.*
Wilson D.N.,Critical Reviews in Biochemistry and Molecular Biology, 2009;44(6): 393-433.*
Maguire B.A., Microbiology and Molecular Biology Reviews, Mar. 2009, p. 22-35.*
Rehm et al.,Clinical Infectious Diseases 2010; 51 (2):176-182.*
Freshney et al.,Culture of Animal Cells, A Manual of Basic Technique, Alan R. Liss, Inc., 1983, New York, p. 4.*
Dermer et al., Bio/Technology, 1994, 12:320.*
Bassetti et al. Annals of Clinical Microbiology and Antimicrobials 2013, 12:22, pp. 1-15.*
Shaffer Yale Journal of Biology and Medicine 86 (2013), pp. 261-270.*
Theuretzbacher et al. Current Opinion in Pharmacology, 2011, 11 : 429-432.*
Kint et al. Trends in Microbiology, Dec. 2012, vol. 20, No. 12, 577-585.*
Becker D.E. Anesth Prog 60:111-123, 2013.*
Babic et al., Drug Resistance Updates 9, 142-156, 2006.*
Paterson et al., Clinical Microbiological reviews 18(40, 657-686, 2005.*
PUBCHEM CID 1556011, pp. 1-11, Date Create Jul. 11, 2005.*
I. Rombel et al., "MgATP Binding and Hydrolysis Determinants of NtrC, a Bacterial Enhancer-Binding Protein", Journal of Bacteriology, 181; 4628-4638, 1999.
S. Roychoudhury et al., "Inhibitors of two-component signal transduction systems: Inhibition of alginate gene activation in Pseudomonas aeruginosa", Proc. Natl. Acad. Sci. 90; 968-969, 1993.
S. Rutheford et al, "AphA and LuxR/HapR reciprocally control quorum sensing in vibrios", Genes & Development, 25; 397-408, 2011.
D. Sack et al., "Getting Serious about Cholera", The New England Journal of Medicine, 355; 649-651, 2006.
S. Schauder et al., "The LuxS family of bacterial autoinducers: biosynthesis of a novel quorum-sensing signal molecule", Molecular Microbiology, 41; 463-476, 2001.
C. Shao et al., "Regulation of Cytotoxicity by Quorum-Sensing Signaling in Vibrio vulnificus is Mediated by SmcR, a Repressor of hlyU", Journal of Bacteriology, 193; 2557-2565, 2010.
Y. Shao et al., "Quorum-sensing non-coding small RNAs use unique pairing regions to differentially control mRNA targets", Molecular Microbiology, 83; 599-611, 2012.

(Continued)

*Primary Examiner* — Venkataraman Balasubramanian
(74) *Attorney, Agent, or Firm* — Meagher Emanuel Laks Goldberg & Liao, LLP

(57) ABSTRACT

Using a whole-cell high-throughput screen, eleven molecules were identified that activate *V. cholerae* quorum sensing (QS). Eight molecules are receptor agonists and three molecules are antagonists of LuxO, the central NtrC-type response regulator that controls the global *V. cholerae* QS cascade. Pro-QS molecules are used for the development of novel anti-infectives.

5 Claims, 13 Drawing Sheets

(56) References Cited

OTHER PUBLICATIONS

Figure 3:
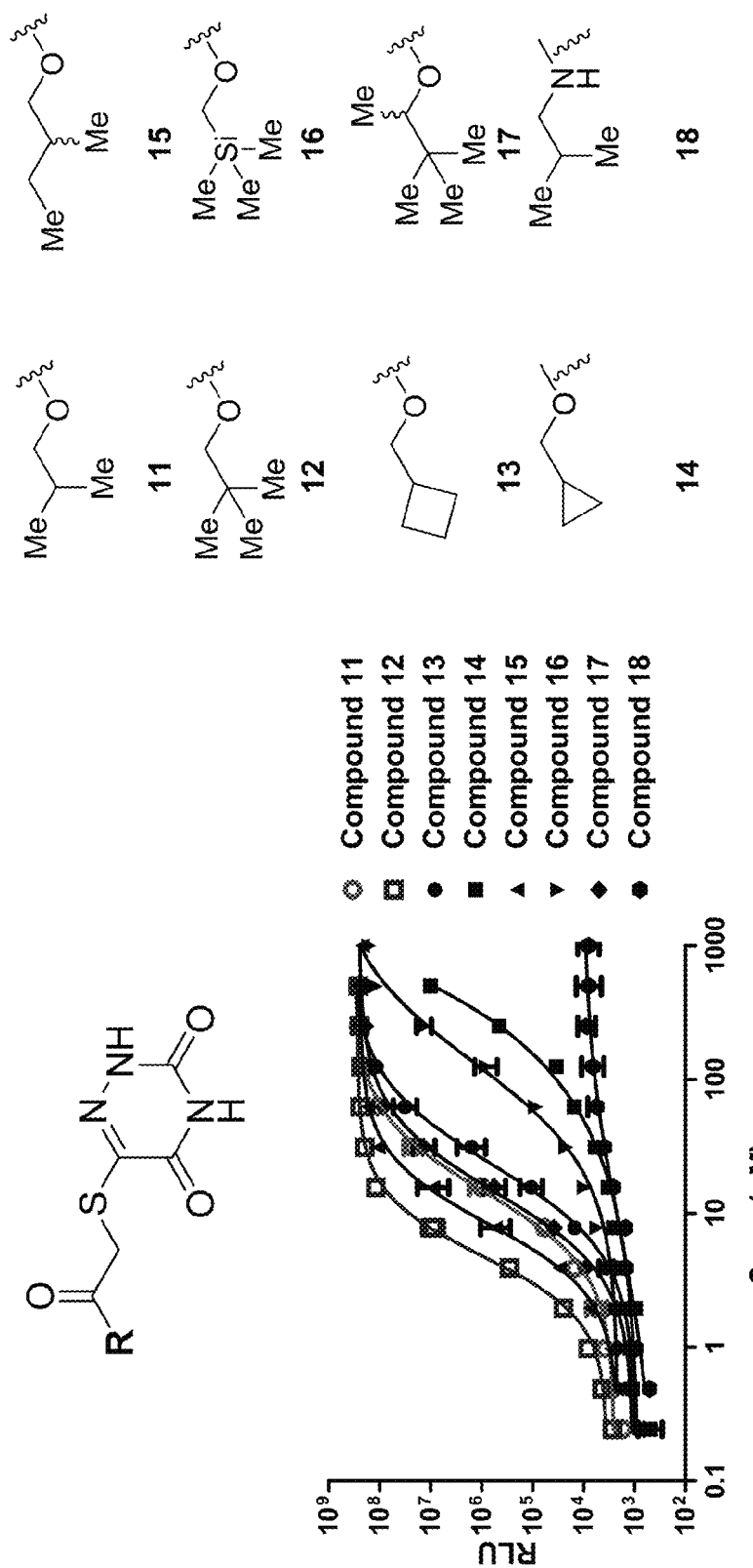
Figure 4:
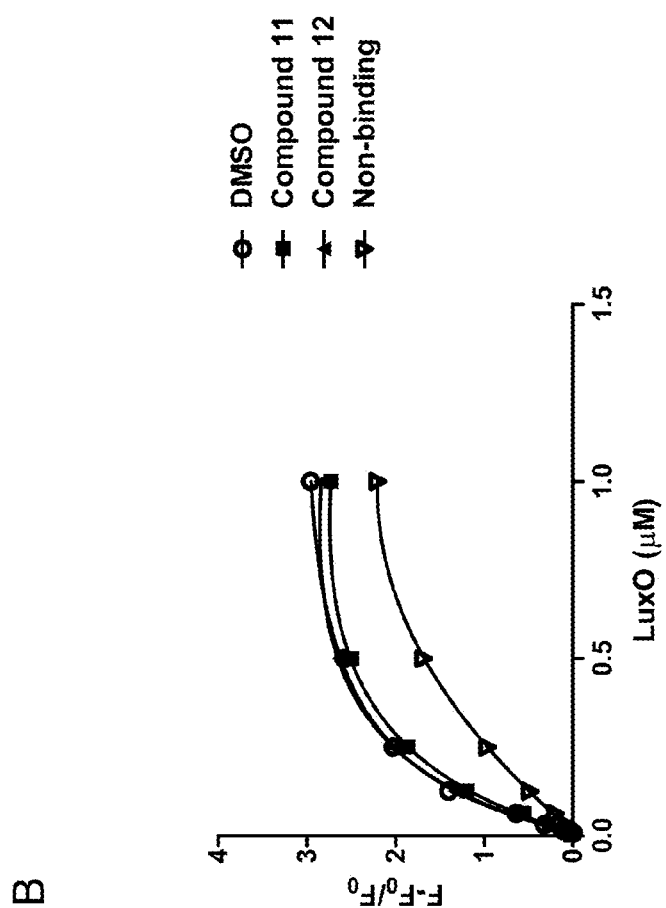
Figure 4:
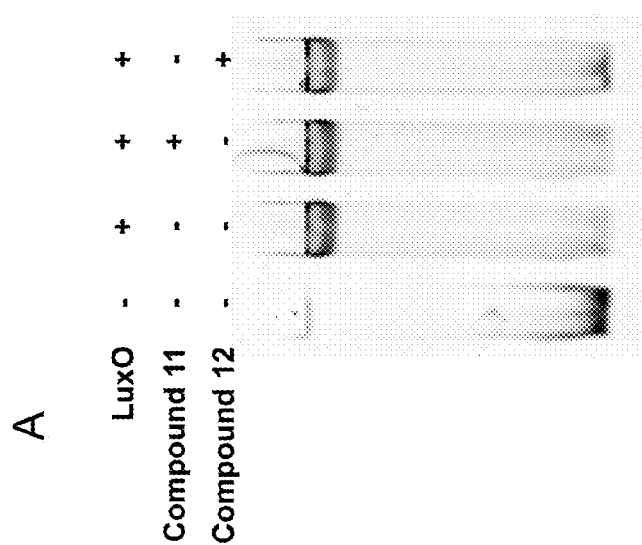
Figure 5:
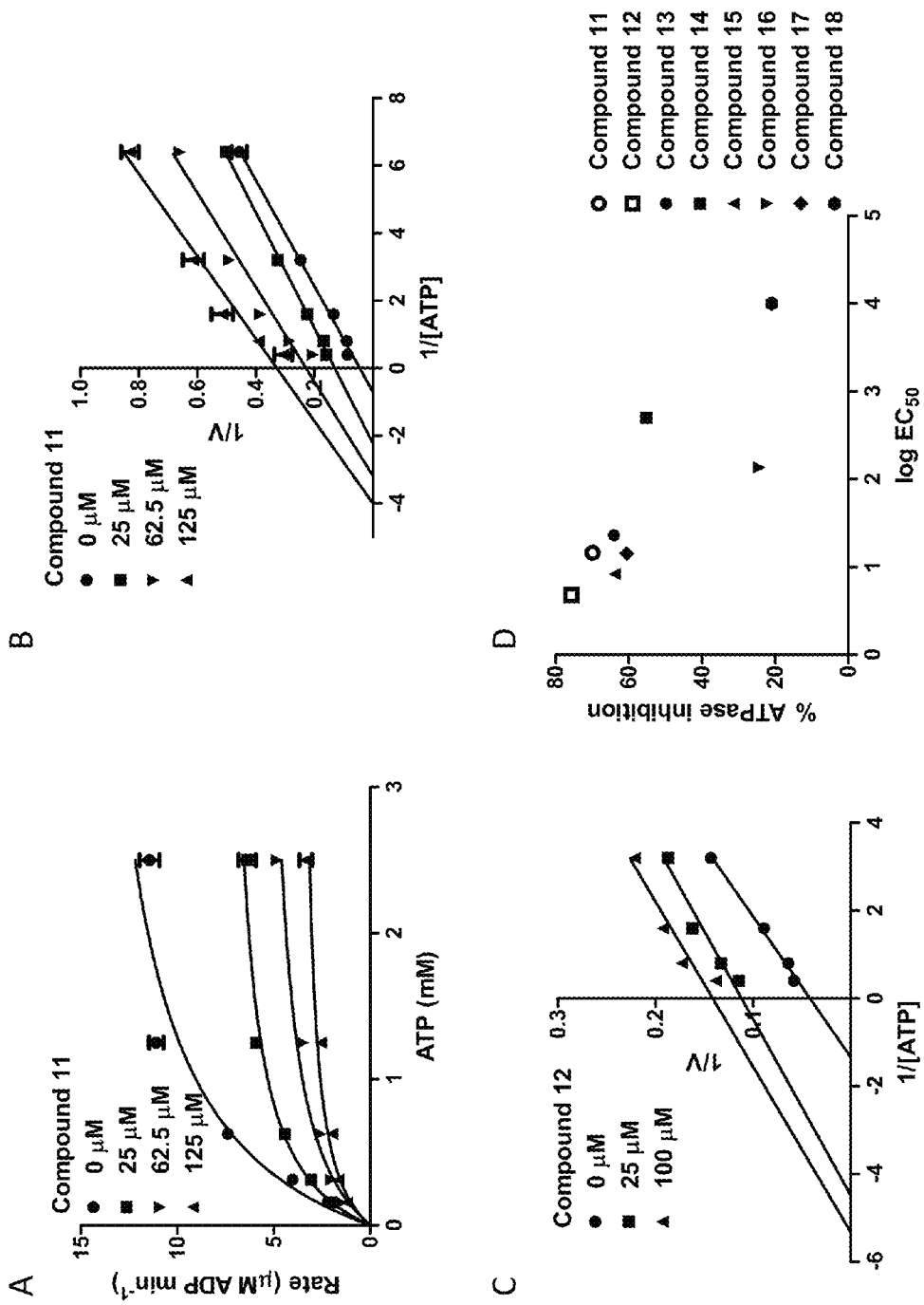
Figure 6:
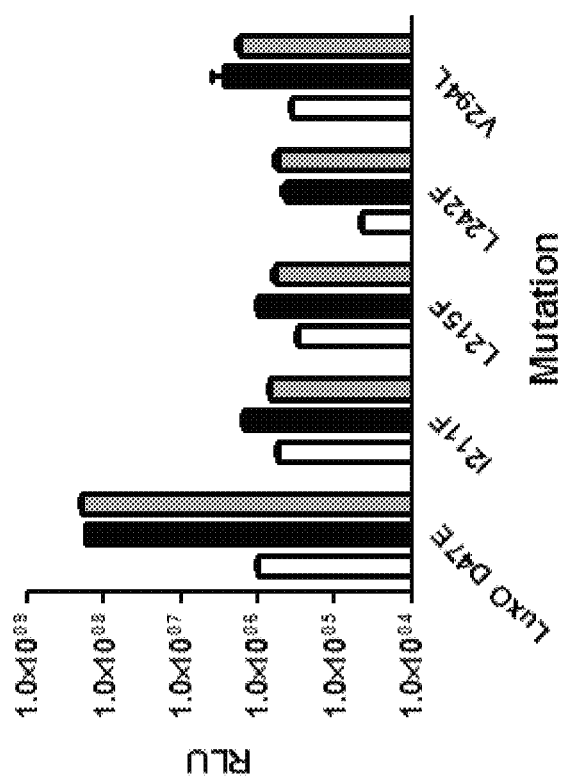

K. Smith et al., "Induction and Inhibition of Pseudomonas aeruginosa Quorum Sensing by Synthetic Autoinducer Analogs", Chemistry & Biology, 10; 81-89, 2003.
K. Stephenson et al., "Developing Inhibitors to Selectively Target Two-Component and Phosphorelay Signal Transduction Systems of Pathogenic Microorganisms", Current Medicinal Chemistry, 11; 765-773, 2004.
K. Stephenson et al., "The Mechanism of Action of Inhibitors of Bacterial Two-component Signal Transduction Systems", The Journal of Biological Chemistry, 275; 38900-38904, 2000.
D. Studholme et al., "Domain Architectures of O52-Dependent Transcriptional Activators", 185; 1757-1767, 2003.
L. Swem et al., "A Quorum-Sensing Antagonist Targets Both Membrane-Bound and Cytoplasmic Receptors and Controls Bacterial Pathogenicity", Mol. Cell., 35; 143-153, 2009.
K. Thelin et al., "Toxin-Coregulated Pilus, but Not Mannose-Sensitive Hemagglutinin, Is Required for Colonization by Vibrio cholerae O1 El Tor Biotype and O139 Strains", Infection and Immunity, 64; 2853-2856, 1996.
K. Tu et al., "Negative Feedback Loops Involving Small Regulatory RNAs Precisely Control the Vibrio harveyi Quorum-Sensing Response", Mol. Cell., 37; 567-579, 2010.
Q. Wang et al., "LuxO controls extracellular protease, haemolytic activities and siderophore production in fish pathogen Vibrio alginolyticus", Journal of Applied Microbiology, 103; 1525-1534, 2007.
Y. Wei et al., "Mechanism of Vibrio cholerae Autoinducer-1 Biosynthesis", ACS Chemical Biology, 6; 356-365, 2011.
F. Yildiz et al., "Molecular analysis of rugosity in a Vibrio cholerae O1 El Tor phase variant", Molecular Microbiology, 53; 497-515, 2004.
J. Zhu et al., "Quorum Sensing-Dependent Biofilms Enhance Colonization in Vibrio cholerae", Developmental Cell, 5; 647-656, 2003.
J. Zhu et al., "Quorum-sensing regulators control virulence gene expression in Vibrio cholerae", PNAS, 99; 3129-3134, 2002.
Ng et al. 'Broad Spectrum Pro-Quorum-Sensing Molecules as Inhibitors of Virulence in Vibrios', PLoS Pathogens, vol. 8(6):1-14, 2012. Entire Document, especially Abstract; Fig 3.
PUBCHEM CID—682135, Create Date: Jul. 8, 2005 {Jul. 8, 2005) p. 1.
Bonnie L. Bassler, E. Peter Greenberg, and Ann M. Stevens, "Cross-Species Induction of Luminescence in the Quorum-Sensing Bacterium Vibrio harveyi", Journal of Bacteriology, 179; 4043-4045, 1997.
Bonnie L. Bassler, Miriam Wright et al., "Intercellular signalling in Vibrio harveyi: sequence and function of genes regulating expression of luminescence", Molecular Microbiology, 9; 773-786, 1993.
Jeffrey L. Bose, Charles S. Rosenberg, Eric V. Stabb, Effects of luxCDABEG induction in Vibrio fischeri: enhancement of symbiotic colonization and conditional attenuation of growth in culture, Arch. Microbiol., 190; 169-183, 2008.
Lynette Cegelski, Garland R. Marshall et al., "The biology and future prospects of antivirulence therapies", Nature Reviews: Microbiology, 6; 17-27, 2008.
Baoyu Chen, Tatyana A. Sysoeva et al., "Engagement of Arginine Finger to ATP Triggers Large Conformational Changes in NtrC1 AAA+ ATPase for Remodeling Bacterial RNA Polymerase", Structure, 18; 1420-1430, 2010.
Guozhou Chen, Lee R. Swem et al., "A strategy for antagonizing quorum sensing", Mol. Cell., 42; 199-209, 2011.
Xin Chen et al., "Structural identification of a bacterial quorum-sensing signal containing boron", Letters to Nature, 415; 545-549, 2002.
T. Chou et al., "Reversible inhibitor of p97, DBeQ, impairs both ubiquitin-dependent and autophagic protein clearance pathways", PNAS, 108; 4834-4839, 2011.
A. Clatworthy et al., "Targeting virulence: a new paradigm for antimicrobial therapy", Nature Chemical Biology, 3; 541-548, 2007.
S. De Carlo et al., "The structural basis for regulated assembly and function of the transcriptional activator NtrC", Genes & Development, 20; 1485-1495, 2006.
F. Duan et al, "Interrupting Vibrio cholerae Infection of Human Epithelial Cells With Engineered Commensal Bacterial Signaling", Biotechnology & Bioengineering, 101; 128-134, 2008.
J. Foster et al. "Kinetic and mechanistic analyses of new classes of inhibitors of two-component signal transduction systems using a coupled assay containing HpkA-DrrA from Thermotoga maritima", Microbiology, 150; 885-896, 2004.
J. Freeman et al., "A genetic analysis of the function of LuxO, a two-component response regulator involved in quorum sensing in Vibrio harveyi", Molecular Microbiology, 31; 665-677, 1999.
C. Fuqua et al., ", Listening in on Bacteria: Acyl-Homoserine Lactone Signalling", Nature Reviews: Molecular Cell Biology, 3; 685-695, 2002.
G. Geske et al., "Expanding dialogues: from natural autoinducers to non-natural analogues that modulate quorum sensing in Gram-negative bacteria", Chemical Society Reviews, 37; 1432-1447, 2008.
C. Gode-Potratz et al., "Quorum Sensing and Silencing in Vibrio parahaemolyticus", Journal of Bacteriology, 193; 4224-4237, 2011.
Y. Gotoh et al., "Novel antibacterial compounds specifically targeting the essential WalR response regulator", The Journal of Antibiotics, 63; 127-134, 2010.
Y. Gotoh et al., "Two-component signal transduction as potential drug targets in pathogenic bacteria", Current in Microbiology, Opinion in Microbiology, 13; 232-239, 2010.
R. Gupta et al., "Structure-Based Design of DevR Inhibitor Active against Nonreplicating *Mycobacterium tuberculosis*", J. Med. Chem., 52; 6324-6334, 2009.
B. Hammer et al., "Quorum sensing controls biofilm formation in Vibrio cholerae", Molecular Microbiology, 50; 101-114, 2003.
J. Henke et al., "Quorum Sensing Regulates Type III Secretion in Vibrio harveyi and Vibrio parahaemolyticus", Journal of Bacteriology, 186; 3794-3805, 2004.
J. Henke et al., "Three Parallel Quorum-Sensing Systems Regulate Gene Expression in Vibrio harveyi", Journal of Bacteriology, 186; 6902-6914, 2004.
M. Hentzer et al., "Attenuation of Pseudomonas aeruginosa virulence by quorum sensing inhibitors", The EMBO Journal, 22; 3803-3815, 2003.
D. Higgins et al., "The major Vibrio cholerae autoinducer and its role in virulence factor production", Nature: Letters, 450; 883-886, 2007.
J. Hilliard et al., "Multiple Mechanisms of Action for Inhibitors of Histidine Protein Kinases from Bacterial Two-Component Systems", Antimicrobial Agents and Chemotherapy, 43; 1693-1699, 1999.
R. Kelly et al., "The Vibrio cholerae quorum-sensing autoinducer CAI-1: analysis of the biosynthetic enzyme CqsA", Nature Chemical Biology, 5; 891-895, 2009.
G. Kovacikova et al., "Regulation of virulence gene expression in Vibrio cholerae by quorum sensing: HapR functions at the aphA promoter", Molecular Microbiology, 46; 1135-1147, 2002.
D. Lenz et al., "The Small RNA Chaperone Hfq and Multiple Small RNAs Control Quorum Sensing in Vibrio harveyi and Vibrio cholerae", Cell, 188; 69-82, 2004.
J. Li et al., "Mutations Affecting Motifs of Unknown Function in the Central Domain of Nitrogen Regulatory Protein C", Journal of Bacteriology, 181; 5443-5454, 1999.
Z. Liu et al., "Mucosal penetration primes Vibrio cholerae for host colonization by repressing quorum sensing", PNAS, 105; 9769-9774, 2008.
G. Lukat et al., "Roles of the Highly Conserved Aspartate and Lysine Residues in the Response Regulator of Bacterial Chemotaxis", The Journal of Biological Chemistry, 266; 8348-8354, 1991.
M. Mattman et al., "Synthetic ligands that activate and inhibit a quorum-sensing regulator in Pseudomonas aeruginosa", Bioorganic & Medicinal Chemistry Letters, 18; 3072-3075, 2008.

(56) References Cited

OTHER PUBLICATIONS

P. Mayville et al., "Structure-activity analysis of synthetic autoinducing thiolactone peptides from *Staphylococcus aureus* responsible for virulence", Proc. Natl. Acad. Sci., 96; 1218-1223, 1999.

L. Carter, "OpaR, a Homolog of Vibrio harveyi LuxR, Controls Opacity of Vibrio parahaemolyticus", Journal of Bacteriology, 180; 3166-3173, 1998.

C. McInnis et al., "Design, synthesis, and biological evaluation of abiotic, non-lactone modulators of LuxR-type quorum sensing", Bioorganic & Medicinal Chemistry, 19; 4812-4819, 2011.

M. Miller et al., "Parallel Quorum Sensing Systems Converge to Regulate Virulence in Vibrio cholerae", 110; 303-314, 2002.

U. Muh et al., "A structurally unrelated mimic of a Pseudomonas aeruginosa acyl-homoserine lactone quorum-sensing signal", PNAS, 103; 16948-16952, 2006.

C. Nadell et al., "The Evolution of Quorum Sensing in Bacterial Biofilms", PLOS Biology, 6; 0171-0179, 2008.

A. Neuwald et al., "AAA+: A Class of Chaperone-Like ATPases Associated with the Assembly, Operation, and Disassembly of Protein Complexes", Genome Research, 27; 27-43, 1999.

W. Ng et al., "Bacterial Quorum-Sensing Network Architectures", Annual Rev. Genet, 43; 197-222, 2009.

W. Ng et al., "Signal production and detection specificity in Vibrio CqsA/CqsS quorum-sensing systems", Molecular Biology, 79; 1407-1417, 2011.

W. Ng et al., "Probing bacterial transmembrane histidine kinase receptor-ligand interactions with natural and synthetic molecules", PNAS, 107; 5575-5580, 2010.

J. Njoroge et al., "Jamming bacterial communication: New approaches for the treatment of infectious diseases", EMBO Molecular Medicine, 1; 201-210, 2009.

R. Novick et al., "Quorum Sensing in Staphylococci", Annual Review of Genetics, 42; 541-564, 2008.

T. Ono et al., "Identification of Proteins Secreted via Vibrio parahaemolyticus Type III Secretion System 1", Infection and Immunity, 74; 1032-1042, 2006.

A. Pompeani et al., "The Vibrio harveyi master quorum-sensing regulator, LuxR, a TetR-type protein is both an activator and a repressor: DNA recognition and binding specificity at target promoters", Molecular Microbiology, 70; 76-88, 2008.

D. Rasko et al., "Targeting QseC Signaling and Virulence for Antibiotic Development", Science, 321; 1078-1080, 2008.

D. Rasko et al., "Anti-virulence strategies to combat bacteria-mediated disease", Nature Reviews: Drug Discovery, 9; 117-128, 2010.

J. Roh et al., "Transcriptional Regulatory Cascade for Elastase Production in Vibrio vulnificus", Journal of Biological Chemistry, 281; 34775-34784, 2006.

A. Wedel et al., "The bacterial enhancer-binding protein NTRC is a molecular machine: ATP hydrolysis is coupled to transcriptional activation", Genes & Development, 9; 2042-2052, 1995.

\* cited by examiner

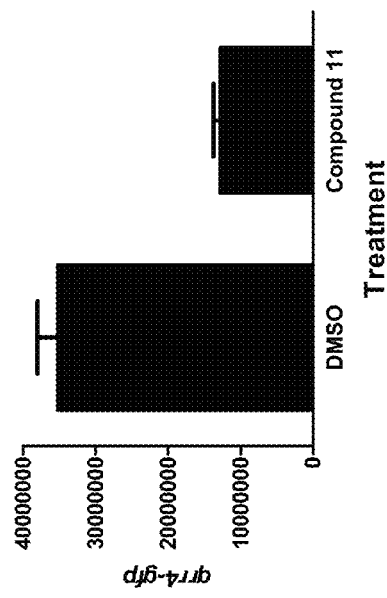
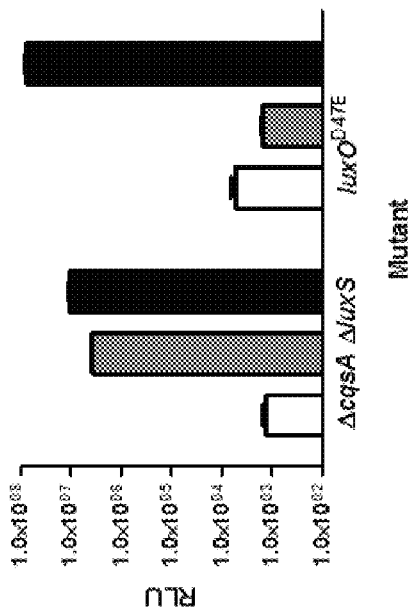
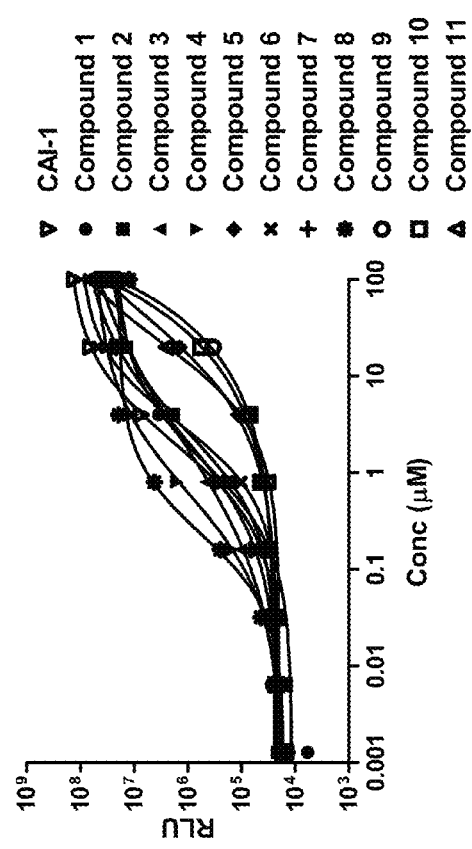
Fig. 2B
Fig. 2C
Fig. 2D

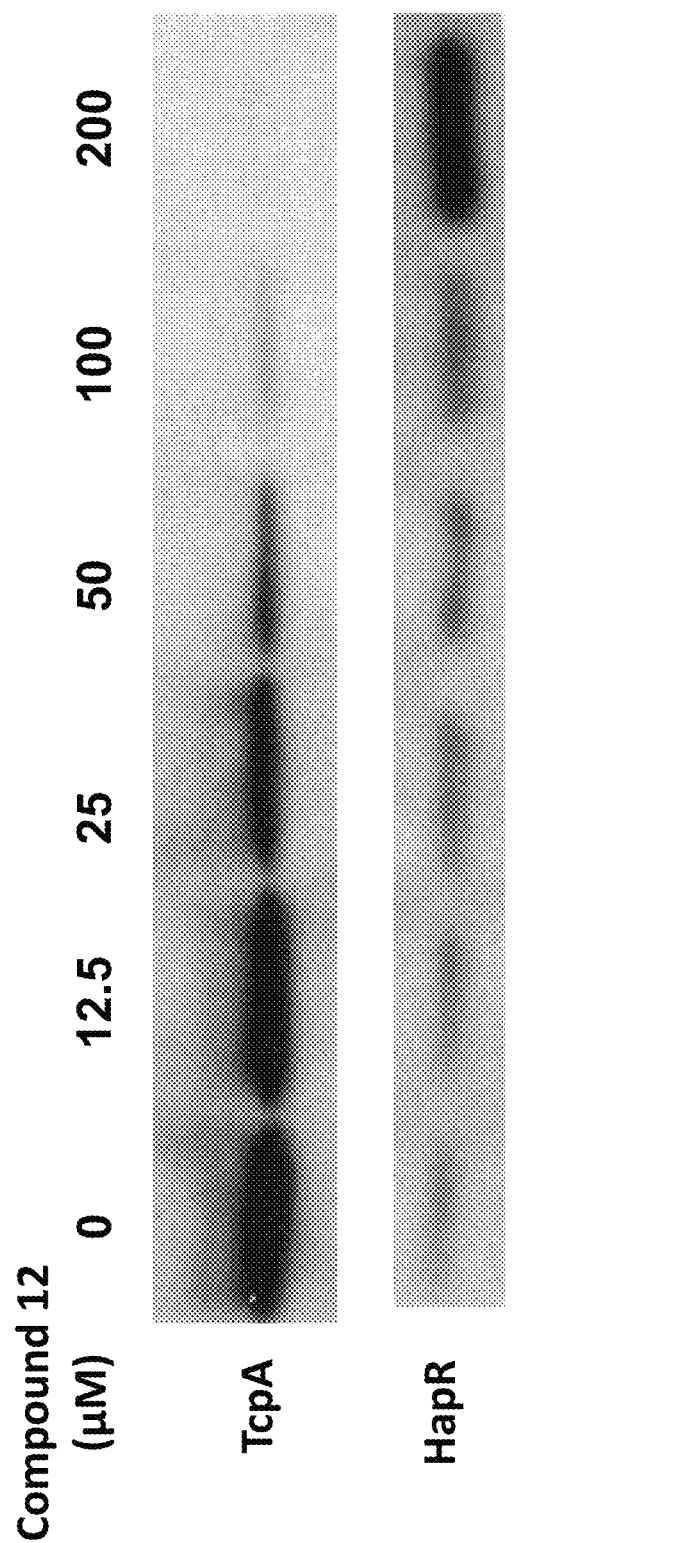

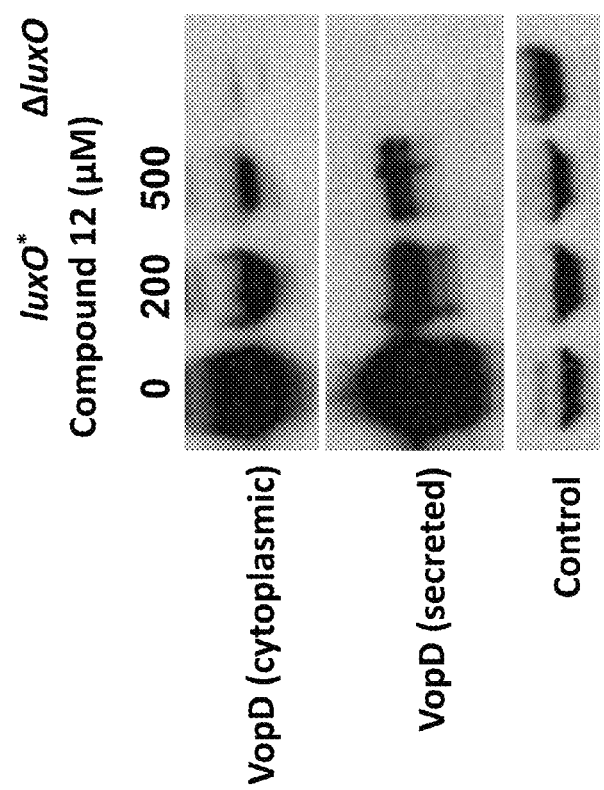
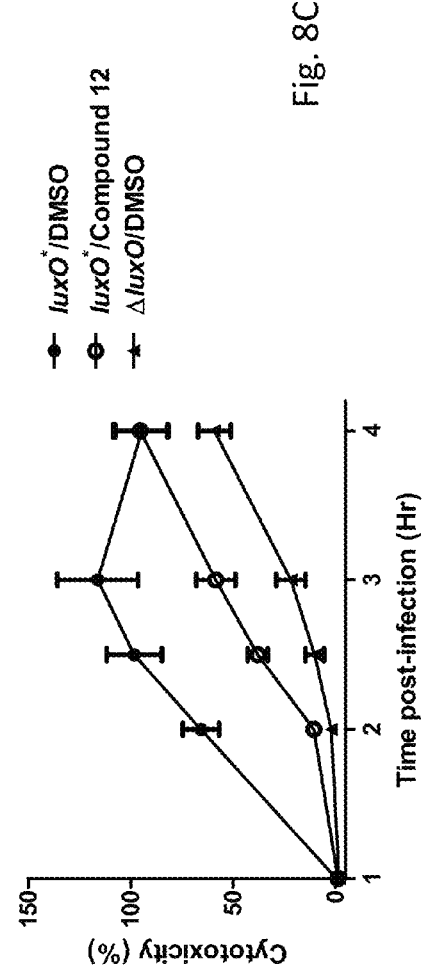
Fig. 8B
Fig. 8C

BROAD SPECTRUM PRO-QUORUM-SENSING MOLECULES AS INHIBITORS OF VIRULENCE IN VIBRIOS

CROSS-REFERENCE TO RELATED APPLICATIONS

This application claims benefit of U.S. Provisional Application No. 61/603,590, filed Feb. 27, 2012, which is hereby incorporated in its entirety by reference.

STATEMENT OF GOVERNMENT INTEREST

This invention was made with government support from NIH#5R01GM0-65859, NIH#5R01AI054442, and NSF# MCB-0343821. The government has certain rights in this invention.

FIELD OF THE INVENTION

The invention relates to compounds that activate quorum sensing in bacteria.

BACKGROUND

Quorum sensing (QS) is a process of bacterial cell-cell communication that relies on the production, release, detection, and response to extracellular signaling molecules called autoinducers. QS allows groups of bacteria to synchronously alter behavior in response to changes in the population density and species composition of the vicinal community. QS controls collective behaviors including bioluminescence, sporulation, virulence factor production, and biofilm formation.

In pathogenic bacteria that cause persistent infections, QS commonly activates virulence factor production at high cell density (HCD). However, in *V. cholerae*, which is the etiological agent of the acute disease cholera, production of HapR regulator at HCD represses genes important for virulence factor production and biofilm formation. This peculiar pattern of virulence gene regulation can be understood in terms of the disease. Following successful *V. cholerae* infection, the ensuing diarrhea washes huge numbers of bacteria from the human intestine into the environment. Thus, expression of genes for virulence and biofilm formation at low cell density (LCD) promotes infection, while repression of these genes by autoinducers at HCD promotes dissemination. Thus, molecules that activate QS have the potential to repress virulence in *V. cholerae*. March et al reported that pretreatment with commensal *E. coli* over-producing the *V. cholerae* autoinducer CAI-1 increased the survival rate of mice following *V. cholerae* infection [66], which further supports the idea of QS potentiators as drugs.

Figure 1:
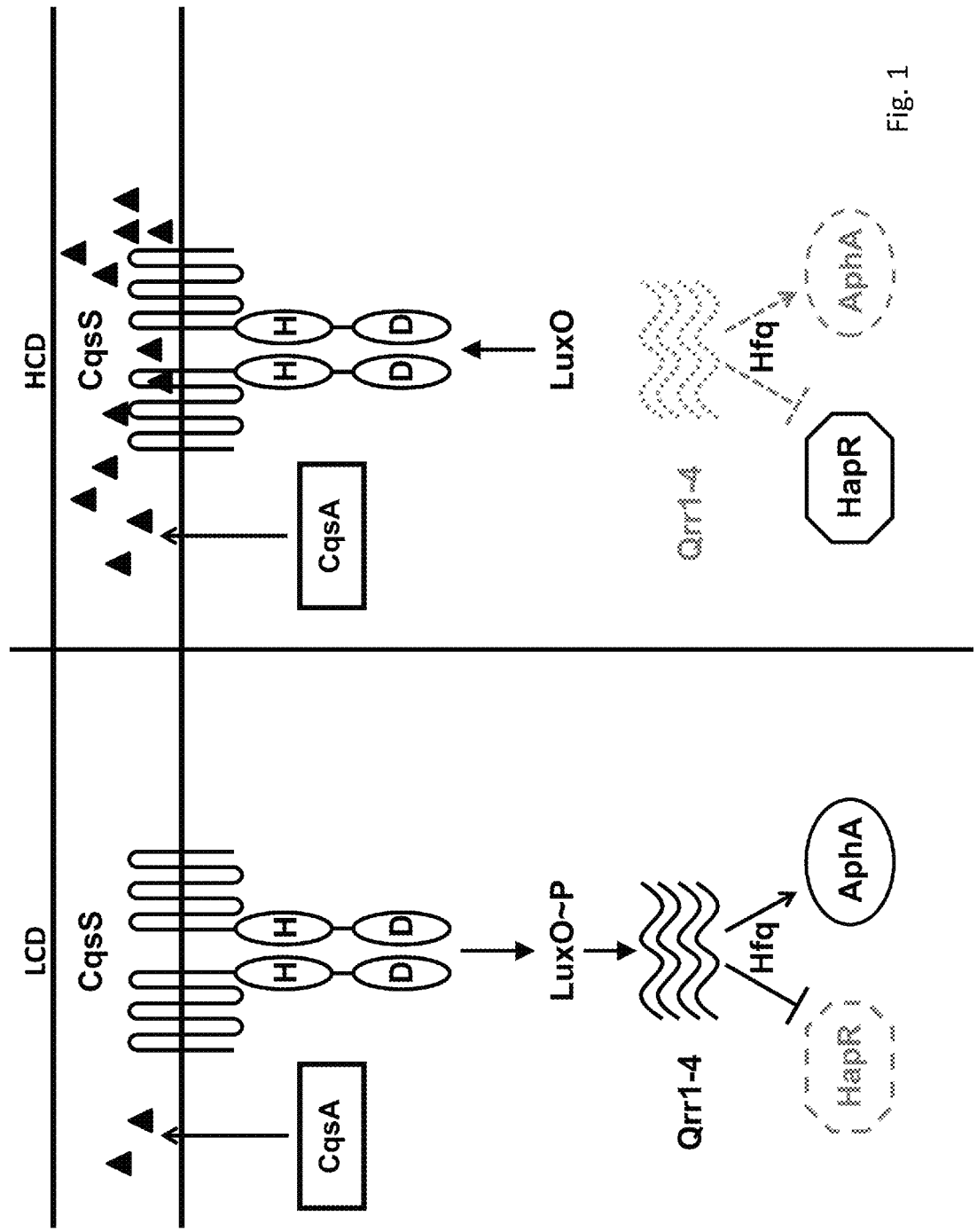

*V. cholerae* produces and detects two QS autoinducer molecules called CAI-1 and AI-2. CAI-1 ((S)-3-hydroxytridecan-4-one) is produced by the CqsA synthase and AI-2 ((2S,4S)-2-methyl-2,3,3,4-tetrahydroxytetrahydrofuran borate) is produced by the LuxS synthase. Detection of CAI-1 and AI-2 occurs through transmembrane receptors CqsS and LuxPQ, respectively. CqsS and LuxPQ are two-component proteins that possess both kinase and phosphatase activities (FIG. 1 shows the CqsA/CqsS system). At LCD, when the receptors are devoid of their respective ligands, their kinase activities predominate, resulting in the phosphorylation of the response regulator LuxO. LuxO~P is the transcriptional activator of four genes encoding small regulatory RNAs (sRNAs), Qrr1-4. The Qrr sRNAs target the mRNAs encoding the quorum-sensing master transcriptional regulators AphA and HapR. At LCD, facilitated by the RNA chaperone Hfq, Qrr1-4 stabilize and destabilize the aphA and hapR mRNA transcripts, respectively. Therefore, AphA protein is made while HapR protein is not (FIG. 1). When autoinducer concentration increases above the threshold required for detection (which occurs at HCD), binding of the autoinducers to their cognate receptors switches the receptors from kinases to phosphatases (FIG. 1). Phosphate flow through the signal transduction pathway is reversed, resulting in dephosphorylation and inactivation of LuxO. Therefore, at HCD, qrr1-4 are not transcribed, resulting in cessation of translation of aphA and derepression of translation of hapR. This QS circuitry ensures maximal AphA production at LCD and maximal HapR production at HCD. AphA and HapR each control the transcription of hundreds of downstream target genes. Hence, reciprocal gradients of AphA and HapR establish the QS LCD and HCD gene expression programs, respectively (FIG. 1).

Targeting response regulators as a broad-spectrum anti-infective strategy has been considered challenging because response regulator functions, such as phosphorylation and DNA binding, are thought to be specific. In spite of this, a handful of molecules that inhibit particular response regulator functions have been reported. Three inhibitors have been identified that target non-NtrC type response regulators, AlgR1 of *Pseudomonas aeruginosa* [50], WalR in low-GC Gram-positive bacteria [51], and DevR in *Mycobacterium tuberculosis* [52]. The molecules function by perturbing phosphorylation (AlgR1 and WalR) and DNA binding (DevR). Walrycins, molecules that inhibit the phosphorylation of the essential WalR response regulator, are active in suppressing growth in multiple Gram-positive bacteria.

LuxO, which is a member of the NtrC family of two-component response regulators, possesses an N-terminal regulatory receiver domain, a central ATPase domain (AAA+type), and a C-terminal DNA-binding domain. Two-component signaling (TCS) proteins are widely distributed in bacteria. In addition to their global importance in microbial physiology, the absence of TCSs in mammalian cells makes them attractive drug targets in pathogenic bacteria. Even though significant effort has been devoted to identifying novel TCS inhibitors, to date, none has been developed into a new class of anti-infective. Problems such as undesirable properties associated with lead molecules have been encountered [56,57]. In particular, inhibitors that generally target the conserved hydrophobic kinase domains of TCS histidine kinases suffer from drawbacks such as low cell permeability, poor selectivity, and unfavorable non-specific off-target effects (e.g. membrane damaging) [58,59,60]. By contrast, approaches to target the sensory domains of histidine kinases have yielded a handful of promising TCS inhibitors. For instance, LED209, an antagonist of the QseC histidine kinase, which regulates motility and pathogenicity in enterohaemorrhagic *E. coli*, reduces virulence in several pathogens both in vitro and in vivo [61]. In addition, in *Staphylococcus aureus*, inhibitory Agr peptide analogs antagonize the AgrC histidine kinase receptors and block abscess formation in an experimental murine model [62].

SUMMARY OF THE INVENTION

Disclosed herein are novel strategies directed at the activation of quorum sensing in *Vibrio* species, and *Vibrio cholerae* particularly, thereby inhibiting the virulence of these bacteria and diminishing the likelihood of infection.

Because QS controls virulence in many clinically relevant pathogens, disrupting QS is viewed as a promising therapeutic strategy for all these pathogens.

Also disclosed are virulence inhibitor molecules that display broad-spectrum capability in activation of QS in *Vibrio* species that employ LuxO. The strategies disclosed herein exploit pro-QS molecules for the development of novel anti-infectives. These strategies, and the molecules employed, inhibit the ATPase activity of NtrC-type response regulator. LuxO serves as an example of the NtrC-type response regulator.

*Vibrio* species are among several infectious bacteria known or proposed to utilize a CqsA/CqsS quorum sensing circuit to control the production of virulence factors. Thus, molecules that activate QS in *V. cholerae* have the potential to control pathogenicity in these globally relevant bacteria.

In a first aspect, the invention is a compound from the group consisting of compounds 12, 13, 14, 16, 17 and 18 (FIG. 3). In a second aspect, the invention is a broad spectrum anti-virulence composition comprising a compound from the group consisting of compounds 12, 13, 14, 16, 17 and 18.

In another aspect, the invention is a method for inhibiting virulence of gram negative quorum sensing bacteria that comprise the quorum sensing response regulator LuxO, wherein the method comprises contacting the bacteria with a compound from the group consisting of compounds 12, 13, 14, 16, 17 and 18. In a particular embodiment, the bacteria are *V. cholerae* or *V. parahaemolyticus*. In an alternative aspect, the method for inhibiting virulence of gram negative quorum sensing bacteria that comprise LuxO comprises contacting the bacteria with a compound from the group consisting of compounds 9, 10, 11 and 15 (FIGS. 2A and 3).

In yet another aspect, the invention is a method for prophylactic treatment of a host to inhibit pathogenicity of bacteria that comprise the quorum sensing response regulator LuxO, wherein the method comprises administering to the host a compound from the group consisting of compounds 12, 13, 14, 16, 17 and 18. In an alternative aspect, the method for prophylactic treatment to inhibit bacterial pathogenicity of bacteria that comprise LuxO comprises administering to the host a compound from the group consisting of compounds 9, 10, 11 and 15.

In another aspect, the invention is a method for inhibiting biofilm formation by gram negative quorum sensing bacteria that comprise LuxO, wherein the method comprises contacting the bacteria with a compound from the group consisting of compounds 12, 13, 14, 16, 17 and 18. In an alternative aspect, the method for inhibiting biofilm formation comprises contacting the bacteria that comprise LuxO with a compound from the group consisting of compounds 9, 10, 11 and 15.

BRIEF DESCRIPTION OF THE DRAWINGS

FIG. 1: The Quorum-Sensing Circuit in *Vibrio cholerae*. The CqsA/CqsS signal transduction system is shown. (Left) At low cell density (LCD), the CAI-1 autoinducer concentration is below the detection threshold, and the membrane bound CqsS receptor functions as a kinase. The LuxO response regulator is phosphorylated and it activates the transcription of genes encoding the four Qrr sRNA genes. Aided by the RNA chaperone Hfq, the Qrr sRNAs activate and repress translation of the AphA and HapR proteins, respectively. (Right) At high cell density (HCD), binding of CAI-1 to CqsS inhibits its kinase activity. LuxO is not phosphorylated and transcription of the qrr genes is terminated. Translation of AphA is inhibited and HapR is derepressed. Dotted lines denote components that are not expressed while solid lines represent those that are produced.

FIG. 2: Identification of QS-Activating Compounds in *V. cholerae*. (A) Chemical structures of eleven QS-activating compounds. (B) Differential responses to Class 1 and Class 2 compounds by the *V. cholerae* ΔcqsA ΔluxS double synthase mutant and the luxO$^{D47E}$ mutant. The normalized light (RLU, relative light units) produced was monitored in the absence (white) and presence of Class 1 (gray) or Class 2 (black) compounds. A representative experiment is shown using compound 1 (Class 1) and compound 11 (Class 2) from (A). (C) QS dose-response curves of *V. cholerae*. The normalized light (RLU, relative light units) produced by the *V. cholerae* ΔcqsA ΔluxS mutant carrying the lux operon is plotted as a function of the concentration of the eleven QS-activating compounds shown in (A). The curve that denotes the response to the native autoinducer CAI-1, is the positive control. Error bars are present, but are too small to be observed in the plot. The bars represent standard errors of the mean for three independent trials. (D) Effect of compound 11 on expression of qrr4. Expression of qrr4 was monitored in a *V. cholerae* luxO$^{D47E}$ strain carrying a qrr4-gfp transcriptional reporter. The response is shown in the presence and absence of 50 μM compound 11. Error bars represent standard errors of the mean for three independent trials.

FIG. 3: Structure-Activity-Relationship of LuxO inhibitors. The core chemical structure of the LuxO inhibitors is shown at the top. All analogs possess the identical 6-thio-5-azauracil moiety with modifications in the terminal side chains (denoted R). Variations in the side chain are shown on the right. Normalized light (RLU, relative light units) produced by the *V. cholerae* luxO$^{D47E}$ strain carrying the lux operon is plotted as a function of concentration of the eight different analogs. Error bars are present, but are too small to be observed in the plot. The bars represent standard errors of the mean for three independent trials.

FIG. 4: The LuxO Inhibitor Does Not Affect DNA Binding. LuxO D47E DNA binding in the presence and absence of compounds 11 and 12 was investigated by gel mobility shift assays (A) and fluorescent anisotropy assays (B). In (A), LuxO D47E was present at 1 μM. Compounds 11 and 12 were present at 200 μM. In (B), LuxO D47E was present at the indicated concentrations and compounds 11 and 12 were present at 200 μM. Error bars are present, but are too small to be observed in the plot. The bars represent standard errors of the mean for three independent trials.

FIG. 5: Enzyme Kinetic Analyses of LuxO ATPase Inhibition. (A) Michaelis-Menton enzyme kinetic analysis of LuxO ATPase activity. The LuxO D47E ATP hydrolysis rate is plotted as a function of the concentration of ATP in the presence of the indicated amounts of compound 11. Error bars represent standard errors of the mean for at least three independent trials. (B) Lineweaver-Burk plot derived from the assay described in (A). (C) Lineweaver-Burk plot derived from a LuxO D47E ATPase assay in the presence of the indicated amounts of compound 12. (D) Correlation between % inhibition of LuxO D47E ATPase activity (2.5 mM ATP and 30 μM inhibitors) and $EC_{50}$ of QS-activation potency (derived from FIG. 3) for the different LuxO inhibitors.

FIG. 6: Isolation of LuxO Mutants Resistant to Inhibition. Normalized light (RLU, relative light units) produced by the *V. cholerae* ΔluxO strain carrying luxO$^{D47E}$ and luxO$^{D47E}$ harboring additional mutations in the absence (white) or presence of 100 µM of compound 11 (black) or compound 12 (gray). Error bars represent standard errors of the mean for three independent trials.

Figure 7:
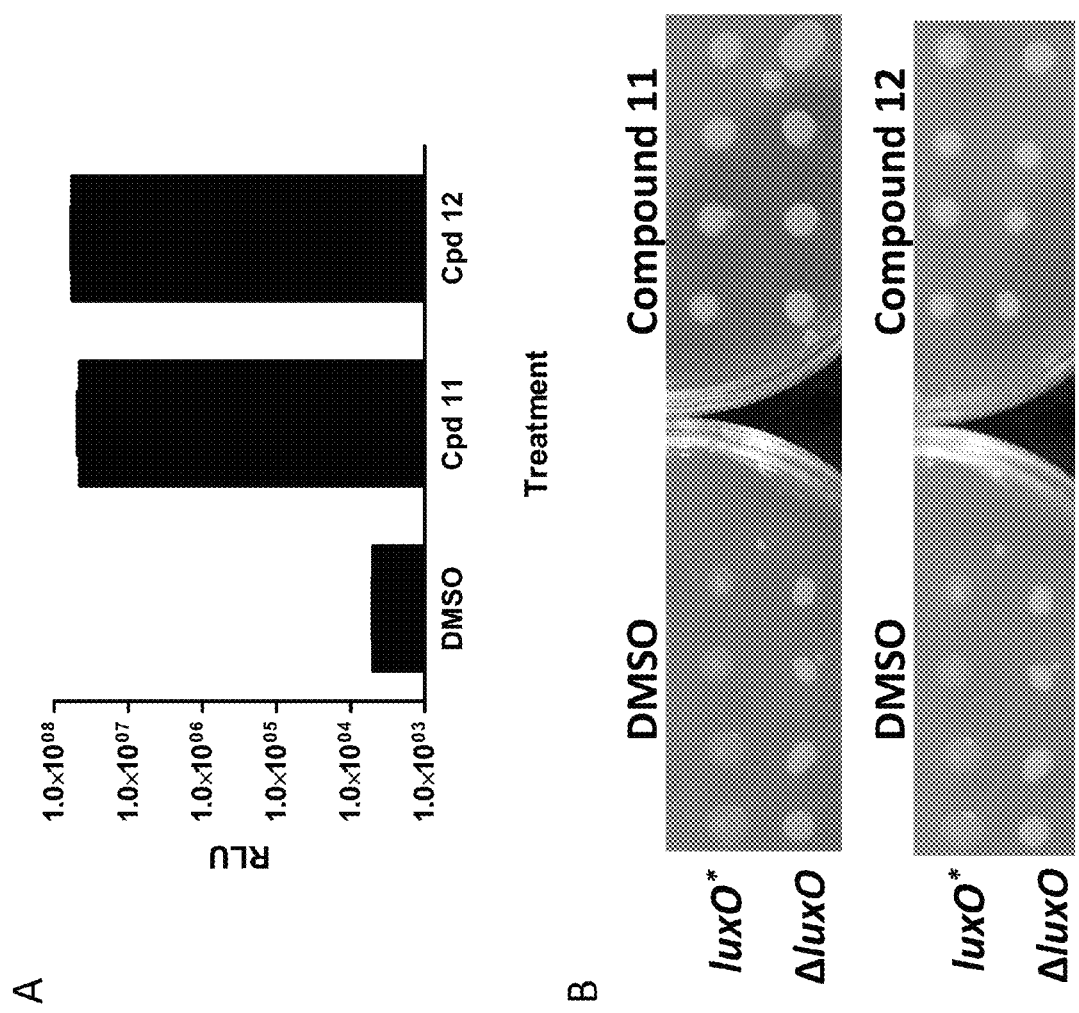

FIG. 7: The LuxO Inhibitors Activate QS in Different *Vibrio* Species. (A) Normalized light (RLU, relative light units) produced by the *V. harveyi* luxO$^{D47E}$ strain in the absence and presence of 50 µM of compounds 11 and 12. (B) Colony morphology of the constitutively active *V. parahaemolyticus* luxO* mutant (LM4476) and the isogenic *V. parahaemolyticus* ΔluxO mutant (LM9688) in the absence and presence of 500 µM compounds 11 and 12. Each strain was inoculated four times on the same plate.

FIG. 8: Control of Virulence Factor Production by LuxO Inhibitors. (A) Western blot analysis of TcpA (Top) and HapR (bottom) in a *V. cholerae* luxO$^{D47E}$ mutant in the presence of 0, 12.5, 25, 50, 100, and 200 µM compound 12. (B) Western blot analysis of the cytoplasmic and secreted VopD in the *V. parahaemolyticus* constitutively active luxO* strain (LM4476) in the presence of 0, 200, and 500 µM compound 12. An isogenic *V. parahaemolyticus* ΔluxO mutant (LM9968) is included as the control. (C) Cytotoxicity of *V. parahaemolyticus* LM4476 (luxO*) on cultured HeLa cells in the absence and presence of 500 µM compound 12. Cytotoxicity was measured by lactate dehydrogenase (LDH) release from HeLa cells. 100% cytotoxicity denotes LDH activity released upon treatment with 0.45% (v/v) Triton-X100. The *V. parahaemolyticus* ΔluxO mutant LM9968 is included for comparison. Error bars represent standard errors of the mean for three independent trials.

Figure 9:
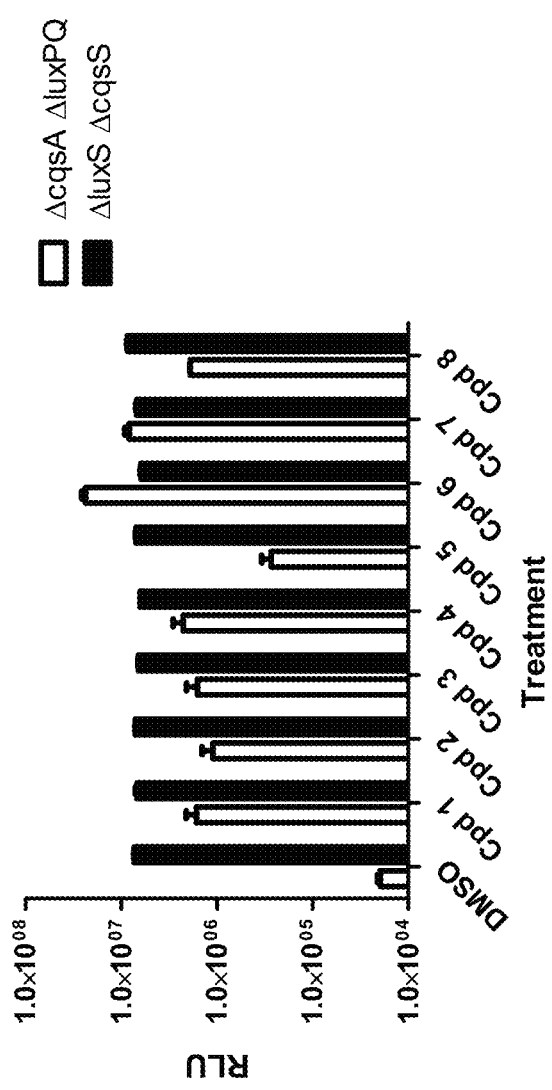

FIG. 9: Responses to Class 1 Compounds by *Vibrio Cholerae* Strains Lacking Each QS Receptor. Normalized light production (RLU) was measured in *V. cholerae* strains lacking either the CqsS or the LuxPQ QS receptor in the presence of 50 µM of the Class 1 compounds. Error bars represent standard errors of means from three independent samples.

Figure 10:
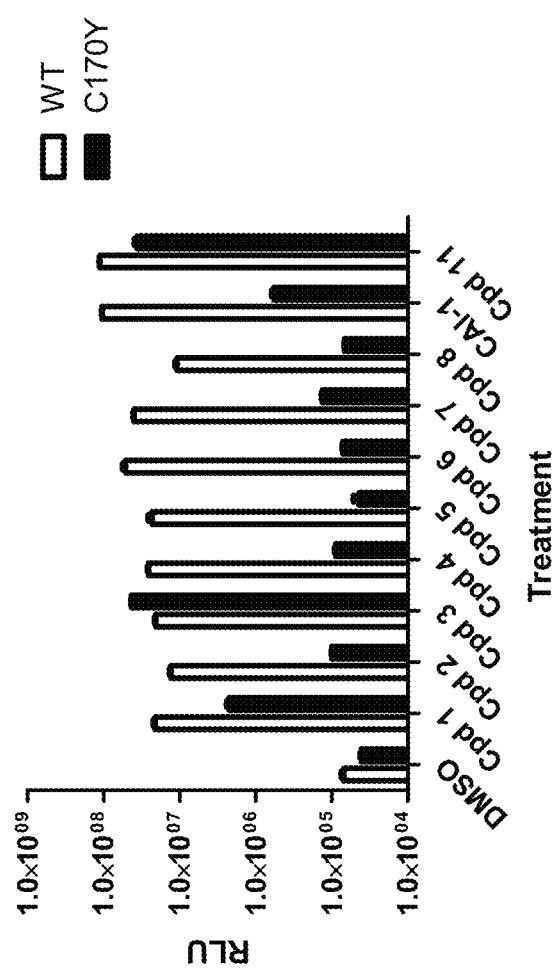

FIG. 10: Responses to Class 1 Compounds by *Vibrio Cholerae* CqsS Mutants with Altered Receptor Specificities. Normalized light production (RLU) was measured in *V. cholerae* strains carrying wild type CqsS or the CqsS$^{C170Y}$ receptor in the presence of 50 µM of the Class 1 compounds. Error bars represent standard errors of means from three independent samples.

Figure 11:
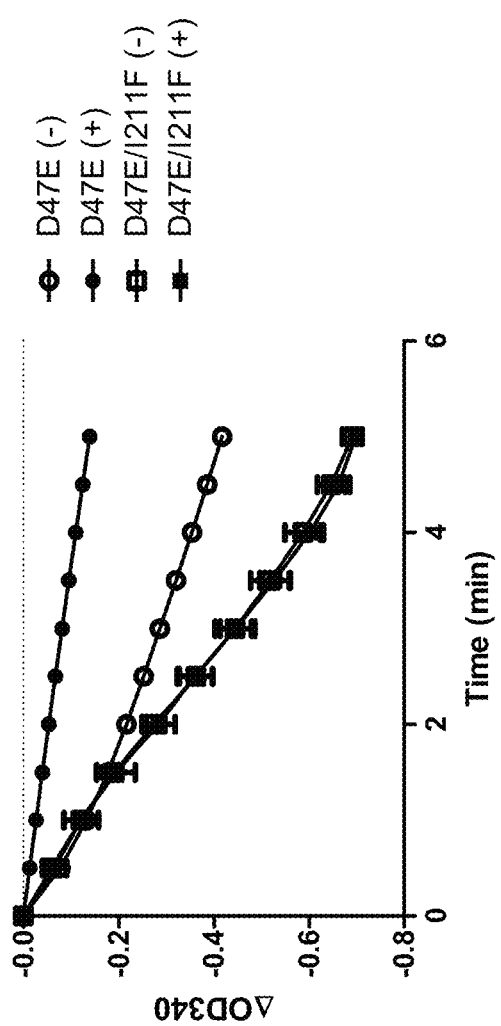

FIG. 11: ATPase Activity of LuxO D47E and LuxO D47E/I211F in the Presence of the LuxO Inhibitors. ATP hydrolysis was measured using a coupled-enzyme assay that monitors changes in absorbance at 340 nm. 100 µM of Compound 12 and 2.5 mM ATP were used in the assay.

DETAILED DESCRIPTION OF THE INVENTION

We identified a set of small molecules that activate the QS system of *V. cholerae*. The QS-activating molecules may be classified as either QS receptor agonists or LuxO inhibitors. The LuxO inhibitors identified here function uncompetitively to perturb LuxO ATPase activity. Genetic analysis of LuxO mutants that are insensitive to the inhibitors suggests that the inhibitors interact with a region adjacent to the ATP binding pocket. Using a set of phenotypic assays, we showed that the inhibitors broadly activate different *vibrio* QS circuits and, in turn, repress virulence factor production and reduce cytotoxicity. Because LuxO is conserved among *vibrio* QS circuits, the molecules we characterize here are capable of inhibiting HSL-based and non-HSL-based *vibrio* QS systems. Numerous NtrC-type proteins homologous to LuxO act in two-component signaling systems and their roles in controlling nitrogen metabolism, virulence, motility, and other important processes have been extensively studied [37]. However, to the best of our knowledge, there exists no previous report of a chemical probe that modulates the activity of a NtrC-family response regulator.

The LuxO inhibitors identified here possess certain favorable drug-like characteristics: potent inhibition, water-solubility, good stability, and cell-permeability. The molecules also display low host-cell cytotoxicity (undetectable cytotoxicity at 500 μM).

Use of pro-QS agents to treat acute infections, in which bacteria use QS to repress virulence is a focus of our invention. We show here that our synthetic pro-QS molecules reduce virulence by inhibiting LuxO. The invention encompasses use of CAI-1, LuxO inhibitors, or other QS-activating molecules as prophylactics to prevent *V. cholerae* or other pathogenic vibrios from initiating the LCD virulence gene expression program that is required for colonization. In this embodiment, inhibiting the launch of virulence factors would provide sufficient time for the host immune system to eliminate the pathogen. In contrast to traditional antibiotics that target essential bacterial processes, growth is not affected by interfering with QS, so development of resistance could potentially be minimized. Thus, just as antagonizing QS in bacteria is an alternative to traditional antibiotics, so is the use of pro-QS agents.

*Vibrio* species detect a wide array of autoinducers (HSLs, CAI-1, and AI-2), thus, molecules that interrupt QS in *Vibrio* species by targeting the cognate receptors/synthases are likely to be autoinducer-specific and will have a limited spectrum. By contrast, because LuxO is nearly identical in all *Vibrio* species, our inhibitors can broadly activate *vibrio* QS irrespective of what type of autoinducer is detected. QS plays an essential role in virulence in other pathogenic vibrios such as *Vibrio parahaemolyticus, Vibrio alginolyticus*, and *Vibrio vulnificus*. The components of the QS circuits in these species are similar to those of *V. cholerae*. Therefore, our invention focuses on QS-activating molecules identified for *V. cholerae* that find broad use for controlling diseases caused by other vibrios. We show here that treatment of *V. cholerae* and *V. parahaemolyticus* with the LuxO inhibitors reduces virulence factor production and impedes cytotoxicity. Thus, our LuxO inhibitors, upon refinement as the particular use requires, can at a minimum be used broadly to control virulence factor production in a variety of *Vibrio* species that use QS to repress pathogenesis.

LuxO belongs to the NtrC protein family, $\sigma^{54}$-binding transcriptional activators that rely on ATP hydrolysis to promote open complex formation. Although these broadly-active LuxO inhibitors are not broad-spectrum NtrC-type inhibitors, our invention encompasses use of the LuxO inhibitors as preliminary scaffolds for building a general NtrC-type response regulator (RR) inhibitor. Structure-activity relationships of the thio-azauracil core, combined with simultaneously screening for molecules that inhibit LuxO and other NtrC type response regulators are envisioned.

The central ATPase module of the NtrC-type RR is classified as AAA+ type [63]. This module is present in multiple domains of life. For example, AAA+ ATPases are important in functions including protein unfolding and degradation (ClpXP, FtsH, and p97), organelle function and maintenance (PEX1 and VPS4), replication and recombination (RuvBL1 and helicases), and intracellular transport (Dyneins). Some eukaryotic AAA+ ATPases have been proposed to be drug targets [64]. Therefore, we contemplate that the thio-azauracil core discovered here can be developed into an inhibitor of AAA+ ATPases across different domains.

The following examples set forth the general procedures involved in practicing the present invention. To the extent that specific materials are mentioned, it is merely for purposes of illustration and is not intended to limit the invention.

Materials and Methods
Bacterial Strains and Culture Conditions

All *V. cholerae* strains are derivatives of wild type C6706str [67]. All *V. harveyi* strains are derivatives of wild type *V. harveyi* BB120 [68]. *V. parahaemolyticus* strains were provided by Dr. Linda McCarter. *Escherichia coli* S17-1 pir, DH5α, and Top10 were used for cloning. The relevant genotypes of all plasmids and strains are provided in Table 1. Unless specified, *E. coli* and *V. cholerae* were grown in LB medium at 37° C. and 30° C. with shaking, respectively. *V. harveyi* and *V. parahaemolyticus* were grown in LM medium at 30° C. with shaking. Colony opacity of *V. parahaemolyticus* was monitored on LM with 2% agar. Unless specified, antibiotic concentrations are as follows: ampicillin, gentamicin, and kanamycin, 100 mg/L; chloramphenicol and tetracycline, 10 mg/L; streptomycin, 5 g/L; polymyxin B, 50 U/L.

TABLE 1

Information on Strains Used[a]

| Strain | Genotype | Plasmid | Reference[b] |
|---|---|---|---|
| *Vibrio cholerae* | | | |
| BH1578 | ΔcqsA ΔluxS | pBB1 | Hammer |
| BH1651 | luxO$^{D47E}$ | pBB1 | Hammer |
| WN1103 | ΔcqsA ΔluxPQ | pBB1 | This study |
| WN1992 | ΔcqsA cqsS$^{C170Y}$ ΔluxPQ | pBB1 | This study |
| DH231 | ΔluxS ΔcqsS | pBB1 | This study |
| SLS353 | luxO$^{D47E}$ | pSLS4 (qrr4-gfp) | Svenningsen |
| WN2442 | ΔluxO | pEVS143-LuxO D47E | This study |
| WN2525 | ΔluxO | pEVS143-LuxO D47E/I211F | This study |
| WN2527 | ΔluxO | pEVS143-luxO D47E/L215F | This study |
| WN2531 | ΔluxO | pEVS143-luxO D47E/V294L | This study |
| WN2579 | ΔluxO | pEVS143-luxO D47E/L242F | This study |
| *Vibrio harveyi* | | | |
| KM83 | luxO$^{D47E}$ | | Tu |
| WN1492 | ΔcqsA ΔcqsS ΔluxN ΔluxPQ | pLAFR-CqsS | Ng |
| WN1834 | ΔcqsA ΔcqsS ΔluxN ΔluxPQ | pLAFR-CqsS F175C | Ng |
| *Vibrio parahaemolyticus* | | | |
| LM4476 | luxO* | | Gode-Potratz |
| LM9688 | ΔluxO | | Gode-Potratz |
| *E. coli* | | | |
| WN133 | BL21 (DE3) | pET28B-LuxO D47E | This study |
| WN2600 | BL21 (DE3) | pET28B-LuxO D47E/I211F | This study |
| WN2181 | BL21 (DE3) | pET28B-NtrC D54E | This study |

[a]The alteration in the luxO$^{D47E}$ allele is Asp61Glu, while other alterations (I211, L215, V294, and L242) in LuxO represent the exactly numbered residue. The luxO$^{D47E}$ allele nomenclature is maintained for consistency in this study and to reflect the nomenclature that is conventionally used in the literature.
[b]References cited in the Table: Gode-Potratz, C. J., and McCarter, L. L. (2011). J Bacteriol 193, 4224-4237. Hammer, B. K., and Bassler, B. L. (2007). Proc Natl Acad Sci USA 104, 11145-11149. Ng, W. L., Wei, Y., Perez, L. J., Cong, J., Long, T., Koch, M., Semmelhack, M. F., Wingreen, N. S., and Bassler, B. L. (2010). Proc Natl Acad Sci USA 107, 5575-5580. Svenningsen, S. L., Waters, C. M., and Bassler, B. L. (2008). Genes Dev 22, 226-238. Tu, K. C., and Bassler, B. L. (2007). Genes Dev 21, 221-233.

Screening for *V. cholerae* QS-Activating Molecules

The 90,000 molecule library was supplied by the High-Throughput Screening Resource Center of the Rockefeller University. The *V. cholerae* strains BH1578 (ΔcqsA ΔluxS pBB1) and BH1651 (luxO$^{D47E}$ pBB1) were grown overnight in LB medium with tetracycline and diluted 25-fold. The diluted cultures were dispensed into 384-well microtiter plates containing screening molecules that were previously added to each well. The final concentration of each compound was ~20 μM. Light production was measured on an Envison Multilabel Reader after 6-hour incubation at 30° C. without shaking. Compounds that induced light production >100-fold were reordered from suppliers and tested.

Bioluminescence Assays for *V. cholerae* and *V. Harveyi*

Overnight cultures of reporter strains were grown in LM medium (for *V. harveyi*) or LB with tetracycline (for *V. cholerae* carrying pBB1) and diluted 20-fold with sterile medium. Bioluminescence and OD$_{600}$ were measured in an Envison Multilabel Reader following 4-hour incubation at 30° C. with shaking. Synthetic molecules were dissolved in DMSO and supplied at varying concentrations to the reporter strains. DMSO was used as the negative control.

Protein Purification

The open reading frame encoding *V. cholerae* LuxO D47E was amplified by PCR and cloned into plasmid pET28B that had been previously digested with NdeI and BamHI. The resulting plasmid was transformed into *E. coli* BL21 Gold (DE3) resulting in strain WN133. Strain WN133 was grown in LB with kanamycin at 30° C. with shaking until the OD$_{600}$ of the culture reached ~1.0. IPTG was added at a final concentration of 200 μM, and the culture was incubated for an additional 4 hours at 30° C. with shaking. Cells were harvested by centrifugation, suspended in lysis buffer (20 mM Sodium phosphate buffer pH 7.4, 0.5 M NaCl, 10% glycerol, and 5 mM imidazole), and lysed using a Cell Cracker. Soluble materials were loaded onto a HiTrap chelating column charged with nickel, the column was washed extensively with lysis buffer, and His$_6$-tagged *V. cholerae* LuxO D47E enzyme was eluted using a linear gradient of increasing concentration of imidazole dissolved in lysis buffer. Fractions containing LuxO D47E were pooled and concentrated with an Amicon Untra-15 filter. Protein was snap-frozen in liquid nitrogen and stored at −80° C. Protein concentrations were determined by UV absorbance at 280 nm. *E. coli* NtrC and other LuxO D47E variants were purified using the same method.

ATPase Assays

A modified coupled-enzyme assay was used to measure the rate of ATP hydrolysis by LuxO D47E [42]. Briefly, ADP released from ATP by LuxO D47E is reacted with phosphoenolpyruvate (PEP) to form pyruvate using pyruvate kinase (PK). Pyruvate is reacted with NADH to form NAD and lactate using lactate dehydrogenase (LDH). The rate of NAD production is followed at 340 nm using a spectrophotometer. ATP hydrolysis rates were inferred from the absorbance change observed ($\epsilon_{NADH,340} - \epsilon_{NAD,340} = 6220$ M$^{-1}$ cm$^{-1}$ for NADH) [42]. The rates of ATP hydrolysis by LuxO D47E were measured in reactions containing 100 mM Sodium phosphate buffer pH 7.4, 5 mM MgCl$_2$, 0.2 mM NADH, 1 mM PEP, 5-20 units of PK/LDH mix (Sigma), and 10 μM LuxO D47E. ATP and inhibitors were added to the reactions at indicated concentrations. The rate of ATP hydrolysis was monitored for 5 minutes. Data were fitted using Graphpad Prism to obtain the kinetic parameters. Percent ATPase inhibition was calculated using the following formula:

$$\left[1 - \frac{Rate_{inhibitor}}{Rate_{DMSO}}\right] \times 100\%$$

DNA Binding Assays

Electrophoretic mobility shift assays to study LuxO and Qrr promoter DNA interactions were performed as described in: Tu K C, et al. [69]. Fluorescence anisotropy assays using LuxO D47E were modified from: Pompeani A J, et al. [70].

Screening for LuxO Mutants Resistant to Inhibitors

The luxO$^{D47E}$ allele was removed from plasmids harbored in WN133 with the enzymes XbaI and BamHI and ligated into pEVS143 [71] that had been previously digested with AvrII and BamHI. The luxO$^{D47E}$ reading frame of the resulting plasmid (WN2029) was randomly mutated using the GeneMorph II Random Mutagenesis Kit. The resulting mutagenized luxO$^{D47E}$ plasmid library was introduced into a $V.$ cholerae $\Delta$luxO strain by conjugation. Individual colonies from this $V.$ cholerae luxO$^{D47E}$ mutant pool were arrayed into 96-well plates containing LB medium with 100 µM compound 12. The $V.$ cholerae $\Delta$luxO strain harboring non-mutated luxO$^{D47E}$ was grown in the absence of compound 12 to provide the reference for background light production. Following overnight static incubation at 30° C., clones that produced light comparable to the background were selected and re-tested in the presence and absence of compounds 11 and 12. DNA sequencing was used to determine the alterations in luxO$^{D47E}$ for inhibitor-resistant mutants. Site-directed mutageneses were performed with the QuikChange II XL Site-Directed Mutagenesis Kit to uncouple multiple mutations.

Western Blot Analysis

Overnight cultures of the $V.$ cholerae luxO$^{D47E}$ strain were diluted 1000-fold in AKI medium containing the indicated concentrations of compound 12. The cultures were statically incubated at 37° C. for 4 hours and subsequently shaken for 4 more hours at 37° C. Cells were collected by centrifugation, TcpA from different samples was analyzed by Western blot as previously described [17]. Overnight cultures of the $V.$ parahaemolyticus luxO* strain (LM4476) were washed and diluted 50-fold in LM medium with 10 mM MgCl$_2$ and 10 mM sodium oxalate in the presence of the indicated concentrations of compound 12. The cultures were grown for 4 hours with shaking at 37° C. Viable cell count showed that all cultures contained ~1×10$^9$ CFU/mL after incubation. Cells were collected by centrifugation, and the secreted and cytoplasmic VopD from different samples were analyzed by Western blot as described in: Henke J M, Bassler B L [47].

Cytotoxicity Assays

Cytotoxicity assays were modified as described in Ono T, et al [48]. HeLa cells (2×10$^4$ cells/well) were cultured for 48 hours at 37° C. and 5% CO$_2$ in a 96-well plate containing DMEM with 10% fetal bovine serum prior to infection. $V.$ parahaemolyticus strains were grown as described above for VopD analysis and used in the infection assays. Immediately prior to $V.$ parahaemolyticus infection, DMSO or compound 12 (500 µM) was added to the HeLa. Serially diluted bacteria were added to HeLa cells at multiplicity of infection of 10. Lactate dehydrogenase release from HeLa cells was assayed between 1-4 hours after infection using the CytoTox 96 nonradioactive cytotoxicity kit (Promega).

Analytical Methods.

NMR spectra were recorded using a Bruker Avance II spectrometer (500 MHz for $^1$H; 125 MHz for $^{13}$C) equipped with either a $^1$H-optimized TCI (H/C/N) cryoprobe or a $^{13}$C-optimized dual C/H cryoprobe. Chemical shifts are reported in parts per million (ppm) and were calibrated according to residual solvent. High-resolution mass spectral analysis was performed using an Agilent 1200-series electrospray ionization—time-of-flight (ESI-TOF) mass spectrometer in the positive ESI mode.

Chemical Reactions.

Unless otherwise noted, all reactions were performed in flame-dried glassware under an atmosphere of nitrogen. All chemicals purchased from commercial vendors were used without further purification. Anhydrous Sure/Seal™ solvents were purchased from commercial vendors.

Purification.

Flash chromatography was performed using C18 Sep-Pak Cartridges from Waters Corporation. Analytical thin-layer chromatography was carried out using Silica G TLC plates, 200 µm with UV$_{254}$ fluorescent indicator (SORBENT Technologies), and visualization was performed by staining (anisaldehyde, ceric ammonium molybdate, or ninhydrin) and/or by absorbance of UV light.

Compound Synthesis.

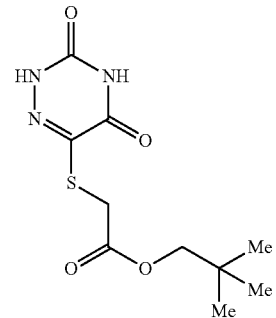 [SMILES: CC(C)(C)COC(=O)CSc1n[nH]c(=O)[nH]c1=O]

General Procedure: Neopentyl 2-((3,5-dioxo-2,3,4,5-tetrahydro-1,2,4-triazin-6-yl)thio)acetate, Compound 12

To 2,2-dimethylpropan-1-ol (260 µL, 2.4 mmol) and Et$_3$N (335 µL, 2.4 mmol) in CH$_2$Cl$_2$ (4.8 mL) at 0° C. was added chloroacetyl chloride (190 µL, 2.4 mmol). The mixture was allowed to stir with warming to ambient temperature over 4 h. and was quenched with H$_2$O (20 mL), extracted with CH$_2$Cl$_2$ (2×20 mL), washed with 1N HCl (20 mL), sat. NaHCO$_3$ (20 mL), brine (20 mL), dried over Na$_2$SO$_4$, and concentrated in vacuo. The resulting colorless oil was used without further purification. To the crude neopentyl 2-chloroacetate (395 mg, 2.4 mmol) in EtOH (2.4 mL) at room temperature was added sodium 3,5-dioxo-2,3,4,5-tetrahydro-1,2,4-triazine-6-thiolate (freshly prepared from 6-mercapto-1,2,4-triazine-3,5(2H,4H)-dione$^1$ (348 mg, 2.4 mmol) and NaOH (115 mg, 2.9 mmol) in H$_2$O (4.8 mL) at room temperature for 1 h.). The resulting mixture was allowed to stir at 40° C. for 14 h. and was diluted with H$_2$O (5 mL) before loading directly onto a 10 g C18 Sep-Pak Cartridge and elution with H$_2$O (25 mL) followed by 1:1 H$_2$O:MeOH (25 mL) to yield neopentyl 2-((3,5-dioxo-2,3,4,5-tetrahydro-1,2,4-triazin-6-yl)thio)acetate as a white solid (127 mg, 19% yield over two steps). $^1$H-NMR (500 MHz, d4-MeOH) δ 3.81 (s, 2H), 3.78 (s, 2H), 0.92 (s, 9H). $^{13}$C-NMR (125 MHz, CDCl$_3$) δ 171.3, 167.1, 161.6, 145.4, 75.9, 32.4, 32.1, 26.8. HRMS (ESI-TOF) calculated for C$_{10}$H$_{15}$N$_3$O$_4$S, 274.0862; observed 274.0860 [M+H]$^+$.

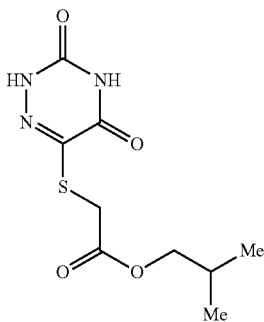 [SMILES: CC(C)COC(=O)CSc1n[nH]c(=O)[nH]c1=O]

Isobutyl 2-((3,5-dioxo-2,3,4,5-tetrahydro-1,2,4-triazin-6-yl)thio)acetate, Compound 11

Prepared following the general procedure from 2-methylpropan-1-ol and 6-mercapto-1,2,4-triazine-3,5(2H,4H)-dione (21 mg, 12% yield over two steps). $^1$H-NMR (500 MHz, d4-MeOH) δ 3.90 (d, J=6.6 Hz, 2H), 3.77 (s, 2H), 1.92 (septet, J=6.7 Hz, 1H), 0.92 (d, J=6.7 Hz, 6H). $^{13}$C-NMR (125 MHz, CDCl$_3$) δ 171.2, 166.0, 160.4, 145.6, 72.8, 32.2, 29.1, 19.5. HRMS (ESI-TOF) calculated for C$_9$H$_{14}$N$_3$O$_4$S, 260.0705; observed 260.0701 [M+H]$^+$.

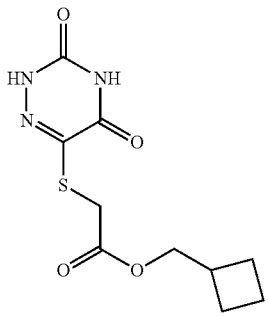 [SMILES: O=C(CSc1n[nH]c(=O)[nH]c1=O)OCC1CCC1]

Cyclobutylmethyl 2-((3,5-dioxo-2,3,4,5-tetrahydro-1,2,4-triazin-6-yl)thio)acetate, Compound 13

Prepared following the general procedure from cyclobutylmethanol and 6-mercapto-1,2,4-triazine-3,5(2H,4H)-dione (16 mg, 9% yield over two steps). $^1$H-NMR (500 MHz, d4-MeOH) δ 4.08 (d, J=6.5 Hz, 2H), 3.31 (s, 2H), 2.67-2.58 (m, 1H), 2.08-1.98 (m, 2H), 1.96-1.71 (m, 4H). $^{13}$C-NMR (125 MHz, CDCl$_3$) δ 171.4, 167.1, 161.5, 145.5, 70.3, 35.6, 32.2, 25.7, 19.3. HRMS (ESI-TOF) calculated for C$_{10}$H$_{14}$N$_3$O$_4$S, 272.0705; observed 272.0700 [M+H]$^+$.

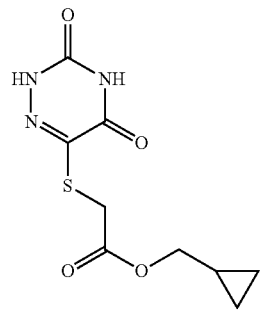 [SMILES: O=C(CSc1n[nH]c(=O)[nH]c1=O)OCC1CC1]

Cyclopropylmethyl 2-((3,5-dioxo-2,3,4,5-tetrahydro-1,2,4-triazin-6-yl)thio)acetate, Compound 14

Prepared following the general procedure from cyclopropylmethanol and 6-mercapto-1,2,4-triazine-3,5(2H,4H)-dione (12 mg, 7% yield over two steps). $^1$H-NMR (500 MHz, d4-MeOH) δ 3.80 (d, J=7.2 Hz, 2H), 3.80 (s, 2H), 1.04-0.93 (m, 1H), 0.45-0.38 (m, 2H), 0.18-0.10 (m, 2H). $^{13}$C-NMR (125 MHz, CDCl$_3$) δ 171.4, 167.2, 161.6, 145.5, 71.5, 32.3, 10.8, 3.8. HRMS (ESI-TOF) calculated for C$_9$H$_{12}$N$_3$O$_4$S, 258.0549; observed 258.0553 [M+H]$^+$.

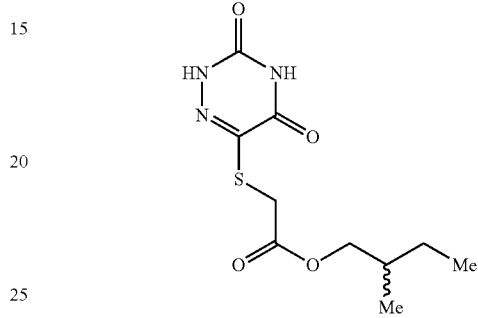

3-Methylbutan-2-yl 2-((3,5-dioxo-2,3,4,5-tetrahydro-1,2,4-triazin-6-yl)thio)acetate, Compound 15

Prepared following the general procedure from (±)-2-methyl-1-butanol and 6-mercapto-1,2,4-triazine-3,5(2H,4H)-dione (47 mg, 21% yield over two steps). $^1$H-NMR (500 MHz, d4-MeOH) δ 4.03-3.89 (m, 2H), 3.75 (s, 2H), 1.74-1.63 (m, 1H), 1.46-1.36 (m, 1H), 1.22-1.11 (m, 1H), 0.92-0.89 (m, 6H). $^{13}$C-NMR (125 MHz, CDCl$_3$) δ 171.4, 167.2, 161.6, 145.5, 71.2, 35.6, 32.2, 27.1, 16.8, 11.7. HRMS (ESI-TOF) calculated for C$_{10}$H$_{16}$N$_3$O$_4$S, 274.0862; observed 274.0858 [M+H]$^+$.

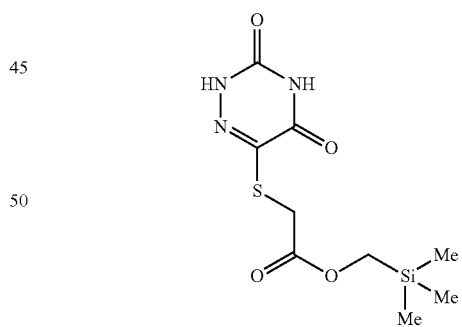

(Trimethylsilyl)methyl 2-((3,5-dioxo-2,3,4,5-tetrahydro-1,2,4-triazin-6-yl)thio)acetate, Compound 16

Prepared following the general procedure from (trimethylsilyl)methanol and 6-mercapto-1,2,4-triazine-3,5(2H,4H)-dione (45 mg, 23% yield over two steps). $^1$H-NMR (500 MHz, d4-MeOH) δ 3.83 (s, 2H), 3.76 (s, 2H), 0.06 (s, 9H). $^{13}$C-NMR (125 MHz, CDCl$_3$) δ 172.0, 167.0, 161.4, 145.5, 60.1, 32.0, −3.0. HRMS (ESI-TOF) calculated for C$_9$H$_{16}$N$_3$O$_4$SSi, 290.0631; observed 290.0627 [M+H]$^+$.

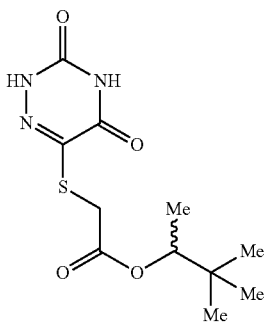 [SMILES: CC(OC(=O)CSc1n[nH]c(=O)[nH]c1=O)C(C)(C)C]

3,3-Dimethylbutan-2-yl 2-((3,5-dioxo-2,3,4,5-tetra-hydro-1,2,4-triazin-6-yl)thio)acetate, Compound 17

Prepared following the general procedure from (±)-3,3-dimethylbutan-2-ol and 6-mercapto-1,2,4-triazine-3,5(2H,4H)-dione (45 mg, 20% yield over two steps). $^1$H-NMR (500 MHz, d4-MeOH) δ 4.66 (q, J=6.4 Hz, 1H), 3.74 (s, 2H), 1.14 (d, J=6.4 Hz, 3H), 0.9 (s, 9H). $^{13}$C-NMR (125 MHz, CDCl$_3$) δ 170.9, 166.9, 161.4, 145.5, 80.6, 35.3, 32.4, 26.2, 15.2. HRMS (ESI-TOF) calculated for $C_{11}H_{18}N_3O_4S$, 288.1018; observed 288.1011 [M+H]$^+$.

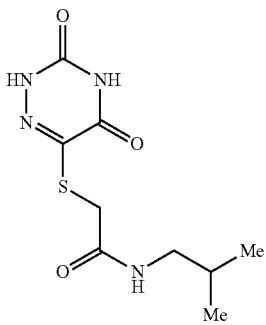 [SMILES: CC(C)CNC(=O)CSc1n[nH]c(=O)[nH]c1=O]

2-((3,5-Dioxo-2,3,4,5-tetrahydro-1,2,4-triazin-6-yl)thio)-N-isobutylacetamide, Compound 18

Prepared following the general procedure from 2-methylpropan-1-amine and 6-mercapto-1,2,4-triazine-3,5(2H,4H)-dione (27 mg, 13% yield over two steps). $^1$H-NMR (500 MHz, d4-MeOH) δ 4.56 (s, 2H), 3.64 (s, 2H), 3.05-2.92 (m, 2H), 1.77 (septet, J=6.6 Hz, 1H), 0.90 (d, J=6.6 Hz, 3H), 0.87 (d, J=6.6 Hz, 3H). $^{13}$C-NMR (125 MHz, CDCl$_3$) δ 171.3, 170.8, 166.8, 159.6, 145.9, 55.1, 48.4, 48.1, 33.7, 29.8, 20.7, 20.6. HRMS (ESI-TOF) calculated for $C_9H_{15}N_4O_3S$, 259.0865; observed 259.0864 [M+H]$^+$.

Results

Identification of Molecules that Activate QS in V. Cholerae

Figure 2A:
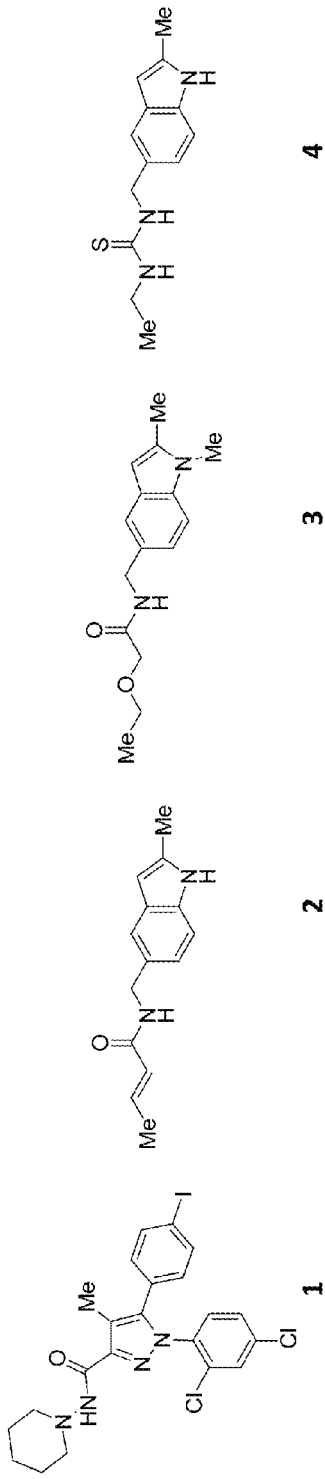
Figure 2A:
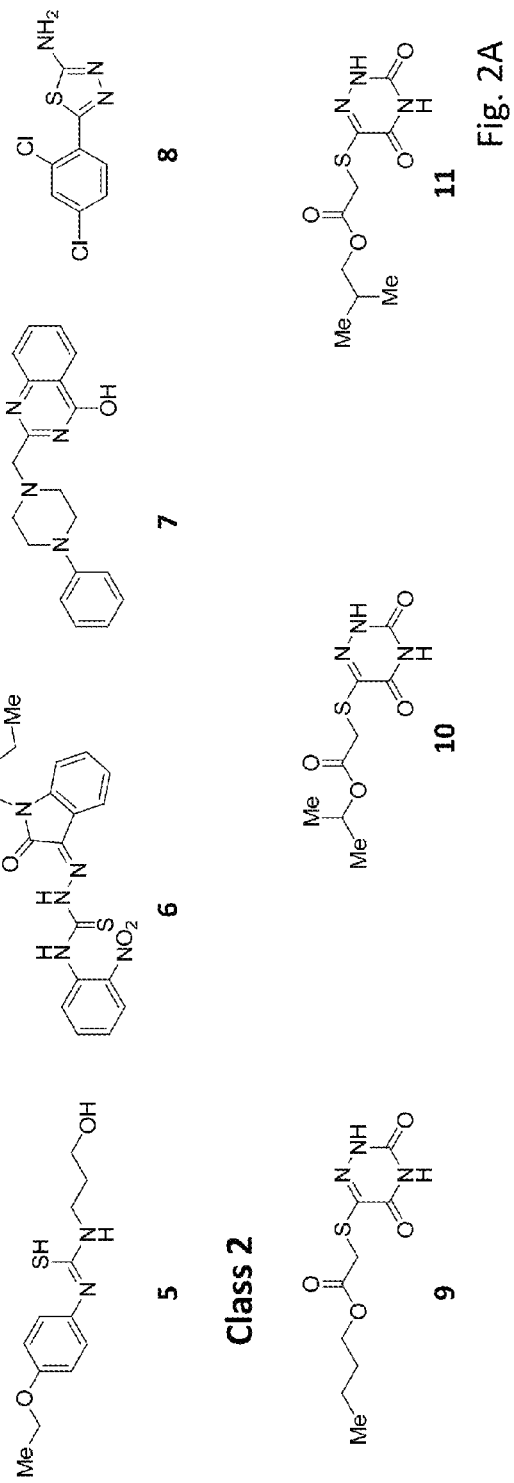

We identified small molecules that activate QS in V. cholerae, in order to induce the HCD state and thus repress virulence factor production. We developed a whole-cell high-throughput screen that relies on QS-dependent induction of bioluminescence (lux) in V. cholerae [22]. We exploited V. cholerae mutants genetically locked into the LCD state and carrying the lux operon to screen for molecules that induce light production, indicating that they activate QS responses. We performed the screen on two different LCD mutants. The first mutant lacks the two autoinducer synthases, CqsA and LuxS. Therefore, both CqsS and LuxPQ QS receptors function as kinases and constitutively phosphorylate LuxO, resulting in repression of HapR. No transcription of the lux operon occurs, and this strain is dark. The second strain carries the luxO$^{D47E}$ allele. This luxO mutation mimics LuxO~P, rendering LuxO constitutively active [23,38]. Therefore, HapR is repressed and the strain is dark. We identified two classes of molecules that could induce light production. Class 1 molecules induce bioluminescence in the double synthase mutant but not in the luxO$^{D47E}$ mutant. These compounds act as QS receptor agonists. Class 2 molecules induce bioluminescence in both the double synthase mutant and the luxO$^{D47E}$ mutant. Class 2 compounds likely target QS components that lie downstream of the receptors. We screened 90,000 molecules and identified eight Class 1 compounds and three Class 2 compounds (FIGS. 2A and 2B). The EC$_{50}$ of Class 1 compounds are comparable to that of CAI-1 and generally lower than those of Class 2 compounds (FIG. 2C). These differences support the idea that the two classes of molecules potentiate QS responses by distinct mechanisms. None of the compounds affected cell growth.

Investigation of the Targets of the QS Activating Compounds

To determine which QS component each compound acts on, we first tested the eight Class 1 compounds against V. cholerae mutants that lack only the CqsS receptor or only the LuxPQ receptor. All eight Class 1 compounds induced light production in the ΔluxPQ strain but not the ΔcqsS strain; hence, these eight molecules function as CqsS agonists (FIG. 9). None has structural homology to the native CAI-1 autoinducer [17,18,39,40].

The three Class 2 compounds that activate QS in both of the LCD screening strains appeared likely to act downstream of the QS receptors. These three compounds are structurally homologous (FIG. 2A); therefore, it appeared likely that they function by an identical mechanism. We focused on the compound displaying the highest potency (i.e., compound 11, FIG. 2B-C). Class 2 compounds could potentially target one or more of the V. cholerae QS cytoplasmic components that function downstream of the receptors: LuxO, σ$^{54}$, Hfq, and/or Qrr1-4. We reasoned that if these compounds interfere with LuxO or σ$^{54}$, transcription of qrr1-4 would decrease in the presence of the inhibitors. By contrast, if the compounds target Hfq or act directly on Qrr1-4, they should not affect qrr1-4 transcription. Results showed GFP production from a qrr4-gfp transcriptional fusion decreased ~3-fold when the luxO$^{D47E}$ strain was treated with compound 11 (FIG. 2D). This result suggested that compound 11 targets either LuxO or σ$^{54}$. If the target of compound 11 is σ$^{54}$, transcription of other σ$^{54}$-dependent genes should be affected when V. cholerae is treated with the compound. We examined transcription of the σ$^{54}$-dependent gene vpsR [41] and found that it did not change significantly in the presence of compound 11. These results suggested that compound 11 targets LuxO.

Structure-Activity-Relationship of Class 2 Compounds

The three identified Class 2 compounds share a 5-thio-6-azauracil core and only their side chains vary (FIG. 2A). In addition, several 5-thio-6-azauracil analogs with other modifications on their side chains displayed weak or no activity in the screen. Therefore, differences in the hydrocarbon side chains must be responsible for the corresponding differences in potency with compounds harboring branched side chains displaying greater potency (i.e., compound 11, FIG. 2C). To explore the relationship between structure and activity, we synthesized a focused library of compounds bearing the conserved 5-thio-6-azauracil core, and we altered the branching in the side chains. We measured activities using bioluminescence in the *V. cholerae* luxO$^{D47E}$ mutant. Several of the side chain modifications decreased potency (as shown by an increase in $EC_{50}$, FIG. 3). However, increasing steric bulk by incorporation of a tert-butyl carbinol side chain led to a 3-fold enhancement in potency (i.e., compound 12, FIG. 3). Thus, the activity of the 5-thio-6-azauracil compounds within this series is highly sensitive to the structural features of the alkyl side chain. In the focused group of molecules we investigated, a bulky, hydrophobic terminal t-butyl moiety is optimal.

Class 2 Compounds Inhibit the LuxO ATPase Activity

NtrC-type response regulators including LuxO possess three biochemical activities: phosphoryl-group accepting activity, DNA-binding activity, and ATP hydrolyzing activity [36]. We investigated which of these activities is inhibited by compounds 11 and 12. First, using whole-cell bioluminescence assays, we found that both compounds activate QS in *V. cholerae* strains expressing either wild type LuxO or LuxO D47E (FIGS. 2B and 3). Wild type LuxO is activated by phosphorylation via the QS cascade, and the LuxO D47E variant, which mimics LuxO~P, while not phosphorylated is constitutively active. Because both wild type LuxO and LuxO D47E are vulnerable to inhibition, it cannot be the ability of LuxO to participate in phosphorylation or dephosphorylation that is impaired by compounds 11 and 12.

To examine if compounds 11 and 12 affect LuxO binding to DNA, we used electrophoretic-mobility-shift and fluorescence anisotropy assays to probe LuxO interaction with qrr promoter DNA. No significant change in LuxO D47E binding to qrr4 promoter DNA occurred in the presence of the inhibitors as judged by mobility shift (FIG. 4A). Quantitative fluorescent anisotropy assays revealed that, in the presence and absence of the LuxO inhibitors, LuxO D47E interacts with the qrr4 promoter DNA with an identical binding constant (~300 nM) (FIG. 4B). Thus, binding to DNA is not altered by the inhibitors.

Finally, we examined whether compounds 11 and 12 affect LuxO ATPase activity. To do this, we used a coupled-enzyme assay [42] to assess the rate of ATP hydrolysis by LuxO in the presence and absence of the compounds. Both compounds inhibit ATP hydrolysis in a dose-dependent manner (FIG. 5A-C). Using traditional Michaelis-Menton enzyme kinetic analyses, we found that both compounds decrease the $K_m$ and the $V_{max}$ of the LuxO ATPase reaction (FIG. 5B-C). The Lineweaver-Burk plots of curves derived from control reactions and from inhibitor-containing reactions display parallel slopes ($K_m/V_{max}$), indicating that compounds 11 and 12 function as uncompetitive inhibitors (FIGS. 5B-C), suggesting they bind to the pre-formed LuxO-ATP complex to inhibit ATP hydrolysis. Indeed, inhibition of LuxO ATPase by the analogs we identified or synthesized (as represented by % inhibition) is correlated with their potency ($EC_{50}$) in inducing QS in the luxO$^{D47E}$ mutant (FIG. 5D). We conclude that the LuxO inhibitors discovered here activate QS in *V. cholerae* by specifically inhibiting the ATPase activity of LuxO. Presumably, in the presence of the inhibitors, LuxO is incapable of participating in open complex formation at the qrr promoters, which prevents transcription of the Qrr sRNAs. In turn, translation of HapR is derepressed and the QS response occurs prematurely.

A Genetic Screen to Identify LuxO Mutants Resistant to Compound 12

It appeared likely that compounds 11 and 12 bind to LuxO at an allosteric site that negatively regulates ATP hydrolysis activity. To determine where compounds 11 and 12 bind, we screened for LuxO mutants refractory to inhibition. To do this, we engineered random mutations into the cloned luxO$^{D47E}$ gene and introduced the mutant library into a *V. cholerae* ΔluxO strain carrying the lux operon. We screened for clones that conferred a dark phenotype in the presence of compound 12, hypothesizing that such mutants harbor alterations in the inhibitor binding-site. Four such mutants were identified (FIG. 6). These LuxO D47E variants are functional, as judged by their ability to repress light production in the absence of inhibitor (FIG. 6). Sequencing revealed that the four LuxO D47E mutants carry L211F, L215F, L242F, or V294L alterations, implicating these residues as important for binding of the inhibitors. We mapped these four alterations on the existing crystal structure of ATP-bound *Aquifex aeolicus NtrC*1 (PDB:3MOE) [43], which displays high sequence homology to LuxO. The four residues we identified in the screen map to three regions that abut the predicted Walker B ATP-binding motif (D245, E246, L247, and C248 in LuxO). In other NtrC-type proteins, mutations in this region have been shown to prevent ATP hydrolysis. Thus, binding of compounds 11 and 12 to this region may induce a conformational change in the nearby ATP-binding pocket that inhibits ATP hydrolysis.

Broad Spectrum Activation of *Vibrio* QS

LuxO is a conserved member of *vibrio* QS circuits. Therefore, compounds 11 and 12 were tested to determine if they could activate QS in other *Vibrio* species. We exploited two well-characterized phenotypes controlled by QS: light production in *V. harveyi* and colony opacity in *Vibrio parahaemolyticus [*44,45,46]. In *V. harveyi*, light production is induced by QS and a *V. harveyi* luxO$^{D47E}$ mutant is dark. Treatment of *V. harveyi* luxO$^{D47E}$ with compounds 11 and 12 induced light production 10.000-fold, indicating that these compounds are indeed active in *V. harveyi* (FIG. 7A). In *V. parahaemolyticus*, the HapR ortholog, OpaR, controls colony opacity. OpaR production is repressed at LCD by LuxO~P via the *V. parahaemolyticus* Qrr sRNAs. *V. parahaemolyticus* mutants that produce low and high levels of OpaR form translucent and opaque colonies, respectively [32,46]. Thus, *V. parahaemolyticus* is naturally translucent at LCD and opaque at HCD. McCarter et al [32] identified a constitutively active LuxO mutant (LM4476, luxO*) in *V. parahaemolyticus* that confers a constitutive translucent colony morphology (FIG. 7B, left). By contrast, an isogenic *V. parahaemolyticus* ΔluxO strain (LM9688) forms opaque colonies (FIG. 7B, left). When the luxO* mutant is plated on medium containing compound 11 or compound 12, the colonies switch from translucent to opaque, a phenotype indistinguishable from the ΔluxO mutant (FIG. 7B, right). These results suggest that compounds 11 and 12 inhibit *V. parahaemolyticus* LuxO from repressing the OpaR-dependent QS program. We conclude that the LuxO inhibitors identified in this study are broadly capable of activating QS in *Vibrio* species that employ LuxO as the central QS regulator.

New Chemical Tools for Controlling Virulence in Vibrios

In pathogenic vibrios, HapR and its homologs (e.g., *V. parahaemolyticus* OpaR and *V. vulnificus* SmcR) function as repressors of virulence factor production at HCD [32,33,34]. For example, in *V. cholerae*, the genes encoding the key *V. cholerae* virulence factors, the CTX toxin and the Toxin Co-regulated Pilus (TCP), are targets of HapR repression at HCD [17,27,30*]. V. parahaemolyticus* uses Type Three Secretion Systems (TTSS) for pathogenesis, and at HCD, OpaR represses the expression of one of the TTSS operons (TTSS-1) [32,47]. Thus, luxO mutants that constitutively produce HapR (*V. cholerae*) or OpaR (*V. parahaemolyticus*) are attenuated in virulence [22,30,32]. The previous section shows that our LuxO inhibitors are active in multiple vibrios. To test whether the inhibitors can disrupt the QS-controlled virulence outputs of pathogenic vibrios, we assayed their effects on TcpA production in *V. cholerae* and production and secretion of VopD, a TTSS-1 effector protein, in *V. parahaemolyticus*. Western blot analysis showed that, in a *V. cholerae* luxO$^{D47E}$ strain, HapR and TcpA levels increased and decreased, respectively, in the presence of compound 12 (FIG. 8A). Likewise, exposing the *V. parahaemolyticus* luxO* mutant to compound 12 resulted in decreased production and secretion of VopD (FIG. 8B).

To test whether repression of these in vitro virulence phenotype translates to repression of the in vivo phenotype, we exploited an established *V. parahaemolyticus* cytotoxicity assay [48] to investigate whether pathogenicity could be inhibited by treatment with the LuxO inhibitors. We infected cultured HeLa cells with the untreated or compound 12-treated *V. parahaemolyticus* luxO* mutant and assayed HeLa cell lysis by measuring lactate dehydrogenase released from the host cytoplasm. At 2 to 3 hours post-infection, HeLa cell lysis was significantly lower in samples infected with the luxO* mutant treated with compound 12 than in samples infected with the luxO* mutant that had not been treated (average cytotoxicity is ~30% and ~100% for treated and untreated, respectively, p<0.01). At that time point, the cytotoxic capability of the Compound 12-treated luxO* mutant is slightly higher than that of the isogenic ΔluxO mutant (FIG. 8C). At 4-hour post-infection, the compound 12-treated luxO* mutant was equally toxic (~100%) as the untreated the luxO* mutant, while the ΔluxO mutant caused only ~60% HeLa cells lysis. Thus, the level of in vitro inhibition of TTSS-1 (FIG. 8B) is a good indicator of the ex vivo inhibition of cytotoxicity (FIG. 8C). The increase in cytotoxicity in Compound 12-treated *V. parahaemolyticus* that occurred at late time points could be due to incomplete inhibition of LuxO, uptake, or degradation of the compound by the HeLa cells. Nonetheless, the progression of *V. parahaemolyticus* killing of mammalian cells is impaired by compound 12, consistent with the notion that virulence factor production can be controlled by small molecule inhibitors of LuxO.

Discussion Of Results

We identified two classes of molecules that activate QS in *V. cholerae*. These newly identified molecules serve two important purposes. First, they can be used as novel chemical probes to study QS signal transduction mechanisms. Second, because QS represses virulence factor production in many pathogenic *Vibrio* species, these molecules, that activate QS, which decreases virulence, have the potential to be anti-virulence agents to combat infectious diseases caused by pathogenic vibrios.

The molecules identified as Class 1 act on the *V. cholerae* CqsS receptor. These molecules, surprisingly, do not resemble the native CAI-1 family of ligands (FIG. 2B). Previous studies revealed that CqsS receptors from different vibrios possess distinct ligand detection specificities. The *V. cholerae* receptor is promiscuous in detecting a range of CAI-1-type molecules, while the *V. harveyi* receptor is relatively stringent [39]. None of the Class 1 molecules identified here activates QS in *V. harveyi*, lending support to the idea that CqsS receptors, although sharing extensive homology, possess different overall stringencies for ligands. We altered a single specificity-determining residue in the *V. cholerae* CqsS receptor (Cys 170) to the corresponding amino acid (Phe) in the *V. harveyi* receptor. This alteration is sufficient to increase stringency in detection of CAI-1 type molecules [39,49], however, it did not abolish detection of the Class 1 molecules (FIG. 10). Identification of CqsS receptor mutants with altered selectivity to the Class 1 molecules will provide additional insight into the molecular basis of ligand-CqsS interactions.

The second class of molecules identified act on LuxO, the central QS regulator that controls transcription of the four Qrr sRNA genes. In contrast to previously identified LuxO inhibitors, our LuxO inhibitor molecules function by an uncompetitive mechanism, presumably by binding to the pre-formed LuxO-ATP complex to prevent ATP hydrolysis. Thus, multiple families of response regulator can be selectively inhibited using small molecules. Furthermore, all three known response regulator activities; phosphorylation, DNA binding, and ATPase, are potential targets for inhibition.

Analyses of LuxO inhibitor-resistant mutants suggest that our inhibitors bind to a region close to the predicted Walker B motif Additional support for this idea comes from studies of other NtrC-type proteins, which show that mutations that affect ATP hydrolysis but do not interfere with ATP binding also map to the Walker B motif and to amino acid residues preceding the conserved GAFTGA domain [43,53,54]. Indeed, one of the LuxO inhibitor-resistant mutations identified here (L242F) lies immediately upstream of the predicted Walker B motif, while both the I211F and L215F mutations map to the helix containing the GAFTGA domain. In addition, the residue identified in the final inhibitor-resistant mutant, V294L, is predicted to sit facing the putative catalytic arginine (R306). The GAFTGA domain is important for interaction with the σ$^{54}$-RNAP holoenzyme [55]. Thus, it was possible that the mutations we isolated in this region (I211F and L215F) suppress inhibition by compounds 11 and 12 by stabilizing the LuxO-σ$^{54}$-RNAP interaction without affecting inhibitor binding. If this were the case, the ATPase activity of the purified LuxO D47E/I211F and D47E/L215F variants would be inhibited by these compounds. However, we purified LuxO D47E/I211F protein and found that the ATPase activity is not inhibited (FIG. 11). This result is consistent with the idea that these mutations abolish inhibitor binding and, in so doing, prevent ATP hydrolysis.

High sequence conservation in the ATPase domain exists between different NtrC-type response regulator family members. We tested whether the LuxO inhibitors could inhibit other NtrC-type response regulators. Compounds 11 and 12 only modestly inhibit (~10%) the ATPase activity of purified *E. coli* NtrC at 250 µM (a concentration at which >80% of the LuxO ATPase activity is inhibited). This finding is surprising because the key residues (I211, L215, L242, and V294) that, when mutated, confer resistance to the inhibitors in LuxO are all present in *E. coli* NtrC. Thus, NtrC must possess additional structural features that render it resistant to inhibition. Structural comparisons between these two related response regulators, coupled with identification of inhibitor-sensitive NtrC mutants, should allow for an understanding of the basis of the differences in inhibitor sensitivity.

In the context of our work, the ATPase domain is highly conserved between all members of the NtrC response regulator family. Therefore, molecules that specifically target the ATPase domain of a single response regulator in this family (e.g., LuxO) could potentially be developed into general inhibitors of NtrC-family of proteins. Because NtrC-type proteins control virulence, nitrogen metabolism, motility, and other vital processes in bacteria [37], targeting the ATPase domain offers an additional route for anti-TCS drug development.

RELATED REFERENCES

1. Ng W L, Bassler B L (2009) Annu Rev Genet. 43: 197-222.
2. Novick R P, Geisinger E (2008) Annu Rev Genet. 42: 541-564.
3. Clatworthy A E, Pierson E, Hung D T (2007) Nat Chem Biol 3: 541-548.
4. Rasko D A, Sperandio V (2010) Nat Rev Drug Discov 9: 117-128.
5. Cegelski L, Marshall G R, Eldridge G R, Hultgren S J (2008) Nat Rev Microbiol 6: 17-27.
6. Hentzer M, Givskov M (2003) J Clin Invest 112: 1300-1307.
7. Geske G D, O'Neill J C, Blackwell H E (2008) Chem Soc Rev 37: 1432-1447.
8. Njoroge J, Sperandio V (2009) EMBO Mol Med 1: 201-210.
9. Fuqua C, Greenberg E P (2002) Nat Rev Mol Cell Biol 3: 685-695.
10. Hentzer M, Wu H, Andersen J B, Riedel K, Rasmussen T B, et al. (2003) EMBO J. 22: 3803-3815.
11. Smith K M, Bu Y, Suga H (2003) Chem Biol 10: 81-89.
12. McInnis C E, Blackwell H E (2011) Bioorg Med Chem 19: 4812-4819.
13. Muh U, Hare B J, Duerkop B A, Schuster M, Hanzelka B L, et al. (2006) Proc Natl Acad Sci USA 103: 16948-16952.
14. Swem L R, Swem DL, O'Loughlin C T, Gatmaitan R, Zhao B, et al. (2009) Mol Cell 35: 143-153.
15. Mattmann M E, Geske G D, Worzalla G A, Chandler J R, Sappington K J, et al. (2008) Bioorg Med Chem Lett 18: 3072-3075.
16. Sack D A, Sack R B, Chaignat C L (2006) N Engl J Med 355: 649-651.
17. Higgins D A, Pomianek M E, Kraml C M, Taylor R K, Semmelhack M F, et al. (2007) Nature 450: 883-886.
18. Kelly R C, Bolitho M E, Higgins D A, Lu W, Ng W L, et al. (2009) Nat Chem Biol 5: 891-895.
19. Chen X, Schauder S, Potier N, Van Dorsselaer A, Pelczer I, et al. (2002) Nature 415: 545-549.
20. Schauder S, Shokat K, Surette M G, Bassler B L (2001) Mol Microbiol 41: 463-476.
21. Henke J M, Bassler B L (2004) J Bacteriol 186: 6902-6914.
22. Miller M B, Skorupski K, Lenz D H, Taylor R K, Bassler B L (2002) Cell 110: 303-314.
23. Lenz D H, Mok K C, Lilley B N, Kulkarni R V, Wingreen N S, et al. (2004) Cell 118: 69-82.
24. Rutherford S T, van Kessel J C, Shao Y, Bassler B L (2011) Genes Dev 25: 397-408.
25. Shao Y, Bassler B L (2012) Mol. Microbiol. 83: 599-611.
26. Hammer B K, Bassler B L (2003) Mol Microbiol 50: 101-104.
27. Kovacikova G, Skorupski K (2002) Mol Microbiol 46: 1135-1147.
28. Liu Z, Miyashiro T, Tsou A, Hsiao A, Goulian M, et al. (2008) Proc Natl Acad Sci USA 105: 9769-9774.
29. Zhu J, Mekalanos J J (2003) Dev Cell 5: 647-656.
30. Zhu J, Miller M B, Vance R E, Dziejman M, Bassler B L, et al. (2002) Proc Natl Acad Sci USA 99: 3129-3134.
31. Nadell C D, Xavier J B, Levin S A, Foster K R (2008) PLoS Biol 6: e14.
32. Gode-Potratz C J, McCarter L L (2011) J Bacteriol 193: 4224-4237.
33. Roh J B, Lee M A, Lee H J, Kim S M, Cho Y, et al. (2006) J Biol Chem 281: 34775-34784.
34. Shao C P, Lo H R, Lin J H, Hor L I (2011) J Bacteriol 193: 2557-2565.
35. Wang Q, Liu Q, Ma Y, Rui H, Zhang Y (2007) J Appl Microbiol 103: 1525-1534.
36. Rombel I, North A, Hwang I, Wyman C, Kustu S (1998) Cold Spring Harb Symp Quant Biol 63: 157-166.
37. Studholme D J, Dixon R (2003) J Bacteriol 185: 1757-1767.
38. Freeman J A, Bassler B L (1999) Mol Microbiol 31: 665-677.
39. Ng W L, Perez L J, Wei Y, Kraml C, Semmelhack M F, et al. (2011) Mol Microbiol 79: 1407-1417.
40. Wei Y, Perez U, Ng W L, Semmelhack M F, Bassler B L (2011) ACS Chem Biol 6: 356-365.
41. Yildiz F H, Liu X S, Heydorn A, Schoolnik G K (2004) Mol Microbiol 53: 497-515.
42. Lukat G S, Lee B H, Mottonen J M, Stock A M, Stock J B (1991) J Biol Chem 266: 8348-8354.
43. Chen B, Sysoeva T A, Chowdhury S, Guo L, De Carlo S, et al. (2010) Structure 18: 1420-1430.
44. Bassler B L, Wright M, Showalter R E, Silverman M R (1993) Mol Microbiol 9: 773-786.
45. Bassler B L, Wright M, Silverman M R (1994) Mol Microbiol 13: 273-286.
46. McCarter L L (1998) J Bacteriol 180: 3166-3173.
47. Henke J M, Bassler B L (2004) J Bacteriol 186: 3794-3805.
48. Ono T, Park K S, Ueta M, Iida T, Honda T (2006) Infect Immun 74: 1032-1042.
49. Ng W L, Wei Y, Perez L J, Cong J, Long T, et al. (2010) Proc Natl Acad Sci USA 107: 5575-5580.
50. Roychoudhury S, Zielinski N A, Ninfa A J, Allen N E, Jungheim L N, et al. (1993) Proc Natl Acad Sci USA 90: 965-969.
51. Gotoh Y, Doi A, Furuta E, Dubrac S, Ishizaki Y, et al. (2010) J Antibiot (Tokyo) 63: 127-134.
52. Gupta R K, Thakur T S, Desiraju G R, Tyagi J S (2009) J Med Chem 52: 6324-6334.
53. Li J, Passaglia L, Rombel I, Yan D, Kustu S (1999) J Bacteriol 181: 5443-5454.
54. Rombel I, Peters-Wendisch P, Mesecar A, Thorgeirsson T, Shin Y K, et al. (1999) J Bacteriol 181: 4628-4638.
55. De Carlo S, Chen B, Hoover T R, Kondrashkina E, Nogales E, et al. (2006) Genes Dev 20: 1485-1495.
56. Stephenson K, Hoch J A (2004) Curr Med Chem 11: 765-773.
57. Gotoh Y, Eguchi Y, Watanabe T, Okamoto S, Doi A, et al. (2010) Curr Opin Microbiol 13: 232-239.
58. Stephenson K, Yamaguchi Y, Hoch J A (2000) J Biol Chem 275: 38900-38904.
59. Hilliard J J, Goldschmidt R M, Licata L, Baum E Z, Bush K (1999) Antimicrob Agents Chemother 43: 1693-1699.
60. Foster J E, Sheng Q, McClain J R, Bures M, Nicas T I, et al. (2004) Microbiology 150: 885-896.
61. Rasko D A, Moreira C G, Li de R, Reading N C, Ritchie J M, et al. (2008) Science 321: 1078-1080.
62. Mayville P, Ji G, Beavis R, Yang H, Goger M, et al. (1999) Proc Natl Acad Sci USA 96: 1218-1223.
63. Neuwald A F, Aravind L, Spouge J L, Koonin E V (1999) Genome Res 9: 27-43.

64. Chou T F, Brown S J, Minond D, Nordin B E, Li K, et al. (2011) Proc Natl Acad Sci USA 108: 4834-4839.
65. Chen G, Swem L R, Swem D L, Stauff D L, O'Loughlin C T, et al. (2011) Mol Cell 42: 199-209.
66. Duan F, March J C (2008) Biotechnol Bioeng 101: 128-134.
67. Thelin K H, Taylor R K (1996) Infect Immun 64: 2853-2856.
68. Bassler B L, Greenberg E P, Stevens A M (1997) J Bacteriol 179: 4043-4045.
69. Tu K C, Long T, Svenningsen S L, Wingreen N S, Bassler B L (2010) Mol Cell 37: 567-579.
70. Pompeani A J, Irgon J J, Berger M F, Bulyk M L, Wingreen N S, et al. (2008) Mol Microbiol 70: 76-88.
71. Bose J L, Rosenberg C S, Stabb E V (2008) Arch Microbiol 190: 169-183.

Various modifications and variations of the invention in addition to those shown and described herein will be apparent to those skilled in the art without departing from the scope and spirit of the invention and fall within the scope of the appended claims. Although the invention has been described in connection with specific preferred embodiments, it should be understood that the invention as claimed should not be unduly limited to such specific embodiments. All publications and patents mentioned in the above specification are incorporated in their entirety by reference.

The invention claimed is:

1. A compound from the group consisting of:

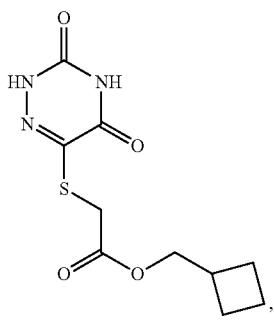

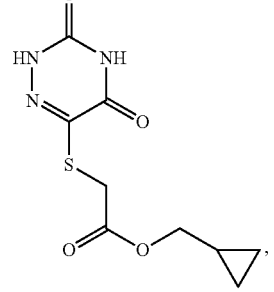

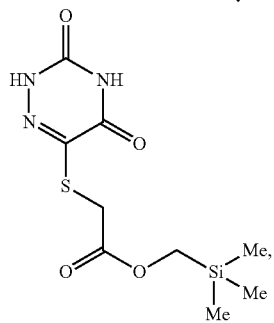

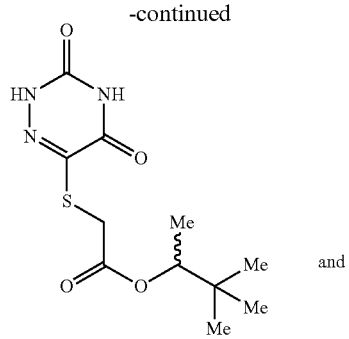

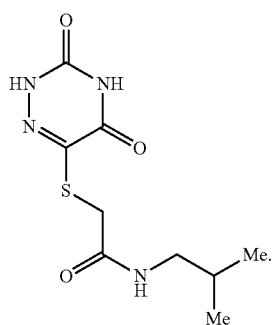

2. A method for inhibiting virulence of gram negative quorum sensing *Vibrio* bacteria that employ the quorum sensing response regulator LuxO, the method comprising contacting gram negative quorum sensing *Vibrio* bacteria that comprise the quorum sensing response regulator LuxO with a compound from a group consisting of

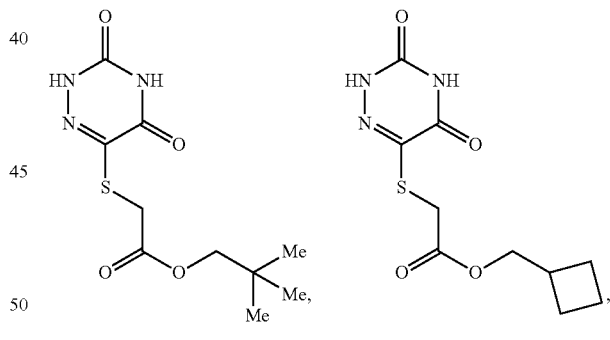

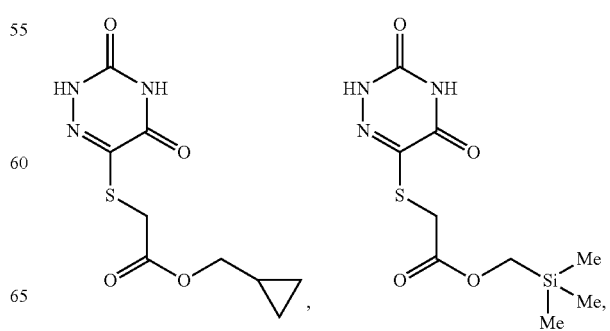

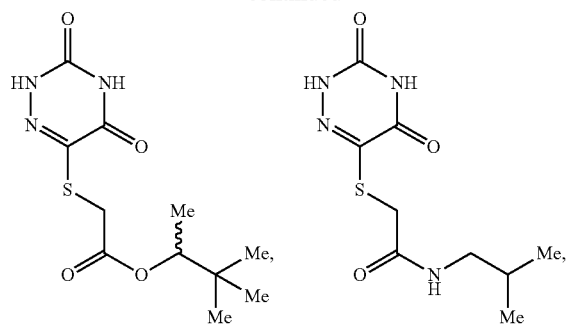
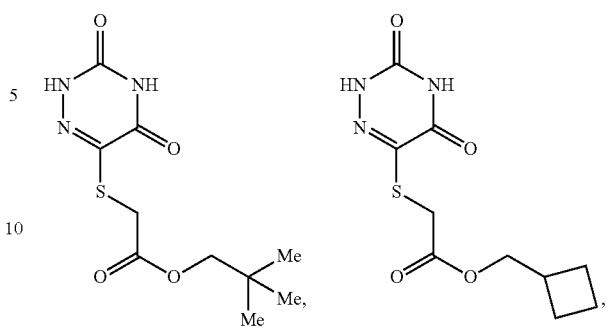
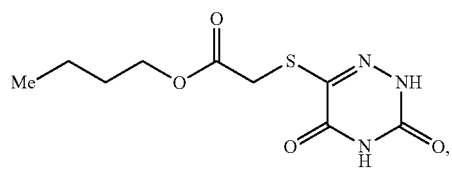
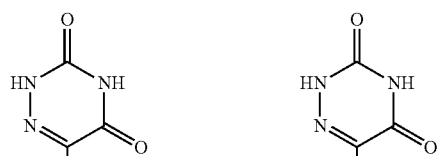
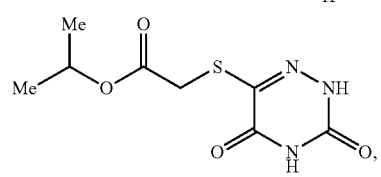
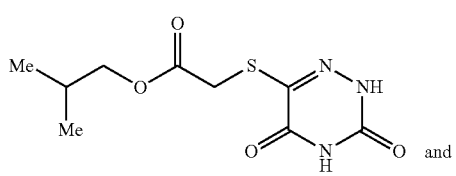
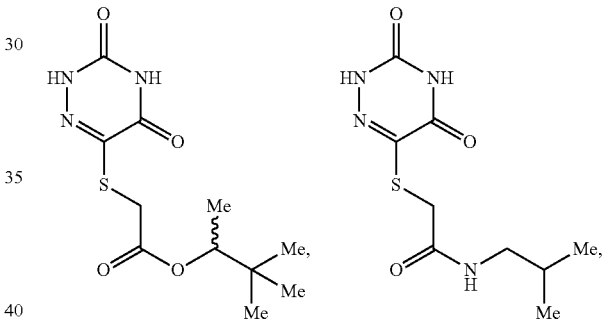
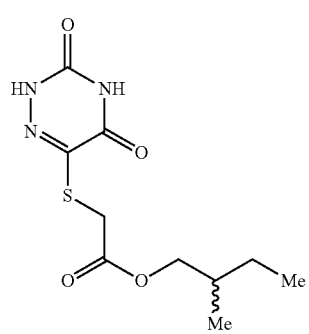 [SMILES: CCC(C)COC(=O)CSc1n[nH]c(=O)[nH]c1=O] and in an amount that inhibits the quorum sensing response regulator LuxO.

3. The method of claim 2 wherein the bacteria are *Vibrio cholerae* or *Vibrio parahaemolyticus*.

4. A method for prophylactic treatment of a host organism, including but not limited to humans, domesticated or wild mammals, domesticated or wild avian species, domesticated or wild fish, and domesticated or wild mollusks, at risk for an imminent and potentially deleterious infection with a member of the *vibrio* species of bacteria, to inhibit bacterial pathogenicity of *Vibrio* bacteria that employ the quorum sensing response regulator LuxO, the method comprising contacting gram negative quorum sensing *Vibrio* bacteria that comprise the quorum sensing response regulator LuxO with a compound from a group consisting of

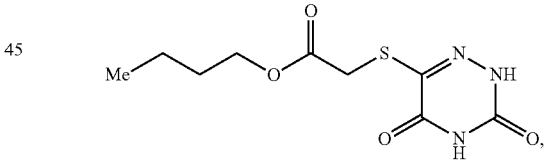
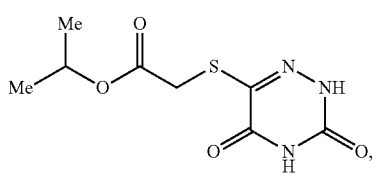
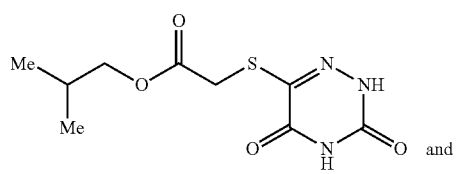 and

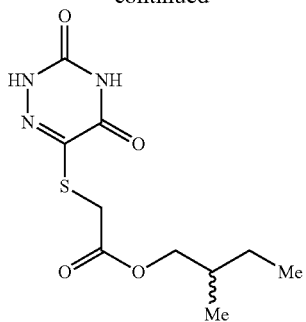

in an amount that inhibits the quorum sensing response regulator LuxO.

5. A method for inhibiting biofilm formation by gram negative quorum sensing *Vibrio* bacteria that employ the quorum sensing response regulator LuxO, the method comprising contacting the *Vibrio* bacteria that comprise the quorum sensing response regulator LuxO with a compound from a group consisting of

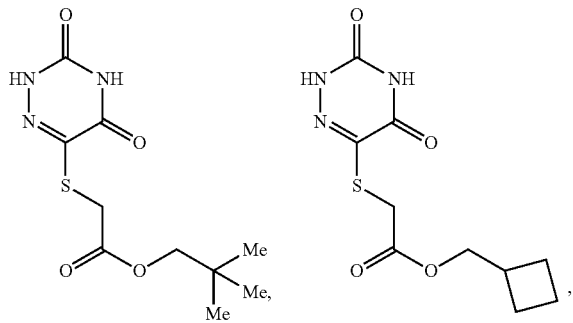

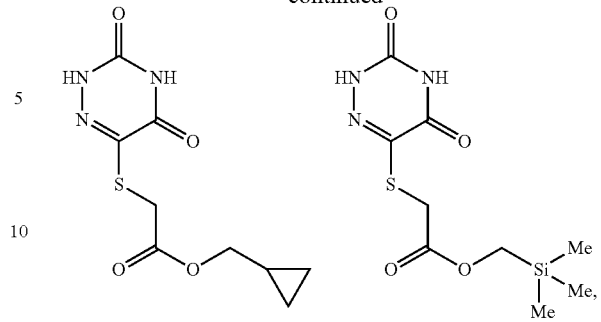

in an amount that inhibits the quorum sensing response regulator LuxO.

* * * * *

UNITED STATES PATENT AND TRADEMARK OFFICE
CERTIFICATE OF CORRECTION

| | | |
|---|---|---|
| PATENT NO. | : 9,573,908 B2 | Page 1 of 1 |
| APPLICATION NO. | : 14/381432 | |
| DATED | : February 21, 2017 | |
| INVENTOR(S) | : Bassler et al. | |

It is certified that error appears in the above-identified patent and that said Letters Patent is hereby corrected as shown below:

In the Specification

Column 1, Line 12, replace:

"STATEMENT OF GOVERNMENT INTEREST
This invention was made with government support from NIH#5R01GM0-65859, NIH#5R01 AI054442, and NSF# 15 MCB-0343821. The government has certain rights in this invention."

With:

-- GOVERNMENT RIGHTS IN THIS INVENTION
This invention was made with government support under Grant Nos. GM065859, and AI054442 awarded by the National Institutes of Health and support under Grant No. MCB0343821 awarded by National Science Foundation. The government has certain rights in the invention. --

Signed and Sealed this
Twenty-eighth Day of March, 2017

Michelle K. Lee
*Director of the United States Patent and Trademark Office*